US008751258B2

(12) United States Patent
Kiuchi et al.

(10) Patent No.: US 8,751,258 B2
(45) Date of Patent: Jun. 10, 2014

(54) INSPECTION ROOM DECISION SUPPORT SYSTEM, INSPECTION ROOM DECISION SUPPORT METHOD AND COMPUTER READABLE MEDIUM

(75) Inventors: Takayoshi Kiuchi, Tokyo (JP); Ryojiro Sasage, Kanagawa (JP); Kunimasa Shimizu, Tokyo (JP); Goro Miura, Tokyo (JP); Koichiro Miyazaki, Tokyo (JP); Shinichi Shidara, Tokyo (JP); Yasuhiro Asai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 404 days.

(21) Appl. No.: 12/894,270

(22) Filed: Sep. 30, 2010

(65) Prior Publication Data
US 2011/0077960 A1    Mar. 31, 2011

(30) Foreign Application Priority Data

Sep. 30, 2009 (JP) ................................ 2009-228666
Aug. 31, 2010 (JP) ................................ 2010-195230

(51) Int. Cl.
*G06Q 50/00* (2012.01)
*G06F 19/00* (2011.01)
*A61B 5/00* (2006.01)
*G06Q 10/00* (2012.01)

(52) U.S. Cl.
USPC .................................................. 705/2; 705/3

(58) Field of Classification Search
USPC ........................................................ 705/2–3
See application file for complete search history.

(56) References Cited

U.S. PATENT DOCUMENTS

| 8,000,979 | B2 * | 8/2011 | Blom ................................ 705/2 |
| 2003/0060678 | A1 * | 3/2003 | Watai et al. .................... 600/109 |
| 2004/0138925 | A1 * | 7/2004 | Zheng ............................... 705/2 |
| 2004/0249670 | A1 * | 12/2004 | Noguchi et al. ................... 705/2 |
| 2006/0007485 | A1 * | 1/2006 | Miyazaki ...................... 358/1.15 |
| 2008/0018436 | A1 * | 1/2008 | Traughber et al. ......... 340/286.07 |
| 2009/0125337 | A1 * | 5/2009 | Abri ................................. 705/3 |
| 2009/0182576 | A1 * | 7/2009 | Warner et al. ..................... 705/2 |
| 2010/0324930 | A1 | 12/2010 | Ueda et al. |

FOREIGN PATENT DOCUMENTS

| JP | 2002-73615 A | 3/2002 |
| JP | 2003-178138 A | 6/2003 |

(Continued)

OTHER PUBLICATIONS

Office Action dated Nov. 26, 2013 issued by the Japanese Patent Office in counterpart Japanese Patent Application No. 2010-195230.

*Primary Examiner* — Joy Chng
(74) *Attorney, Agent, or Firm* — Sughrue Mion, PLLC

(57) ABSTRACT

An inspection room decision support system for providing support in deciding one inspection room in which a requested endoscopic inspection will be conducted, plural inspection rooms, the system includes: an input unit that inputs information; a registration unit that registers at least information about each of the inspection rooms, information about a number of persons waiting for inspection in each of the inspection rooms and information about an endoscope used in each of the inspection rooms into a database in accordance with the information inputted by the input unit; and a control unit which reads at least the information about each of the inspection rooms, the information about the number of persons waiting for inspection in each of the inspection rooms and the information about the endoscope in each of the inspection rooms from the database, and makes a display device display these pieces of information associated with each other.

33 Claims, 12 Drawing Sheets

(56) References Cited

FOREIGN PATENT DOCUMENTS

| JP | 2004-302957 A | 10/2004 |
| JP | 2004-358092 A | 12/2004 |
| JP | 2005044210 A | 2/2005 |
| JP | 2008-129936 A | 6/2008 |
| JP | 2008-212184 A | 9/2008 |
| JP | 2009-134424 A | 6/2009 |
| WO | 2009/104527 A1 | 8/2009 |

* cited by examiner

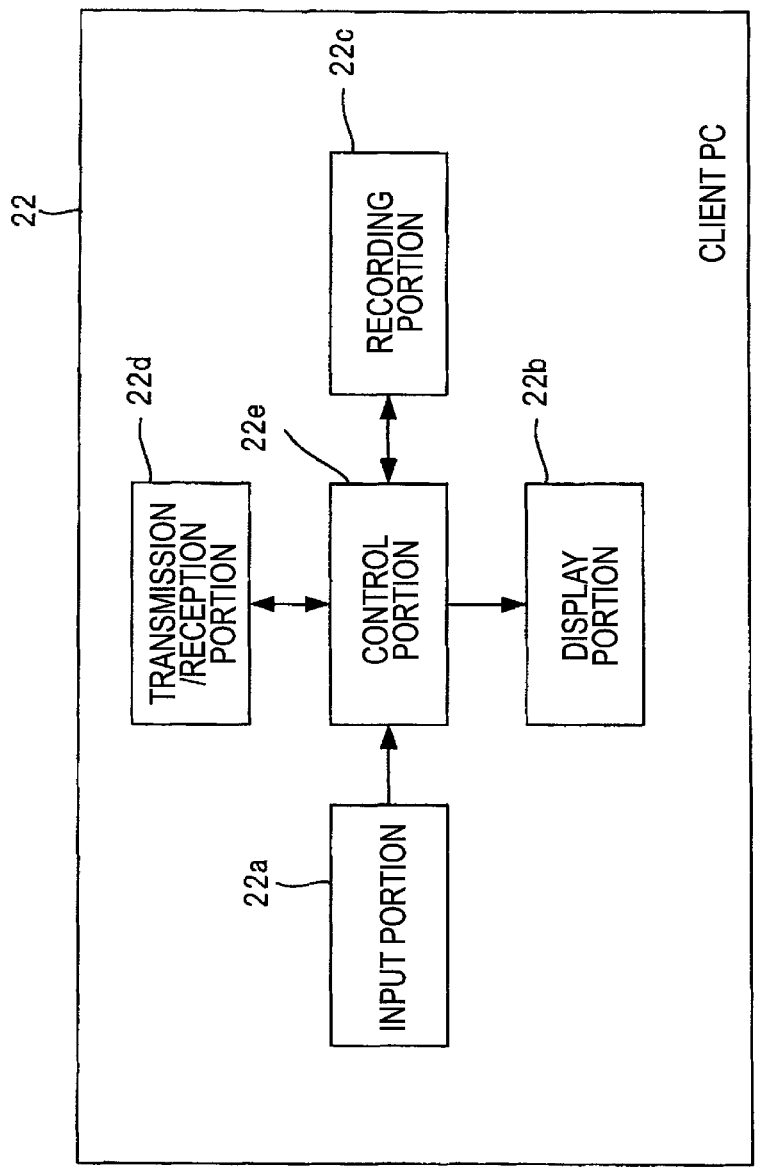

FIG. 4

| | | | | | | | | | | | |
|---|---|---|---|---|---|---|---|---|---|---|---|
| | | | | | | | | | | | |

FUJISUKE FUJI ♂AB(+) PREGNANT
01234  31 YEARS OLD (1977.11.1)
       INPATIENT BUILDING ABC (301)

[RESERVATION DETAILS] [RETRIEVED ORDER LIST] [INTERVIEW/PRE-TREATMENT] [INSPECTION RECORD] [IMAGE CAPTURE/REGISTER] [IMAGE DISPLAY] [REPORT] [PATHOLOGY] [CONDUCT] [OPTION]  — C

[REGISTER RESERVATION] [EDIT RESERVATION]   [CALL] [UNLINK]   [ALLO-CATE]   [PRINT ON ACCEPTANCE] [PRINT RIST] [OUTPUT FILE]

[ACCEPT] [CANCEL]   — B / B1

| VISIT | ACCEPT | INSPECT | BILL | PATIENT ID | NAME | BIRTH DATE | AGE | SEX | ORDER NUMBER | SCHEDULED DATE | SCHEDULED TIME | INPATIENT/OUTPATIENT DISTINCTION | INSPECTION ITEM |
|---|---|---|---|---|---|---|---|---|---|---|---|---|---|
| ○ | | | | 01234 | FUJISUKE FUJI | 1977/11/11 | 31 | MALE | 1111111222222 | 2008/12/11 | 11:30 | INPATIENT | UPPER |
| ○ | ○ | ○ | ○ | 01235 | FUJIO FUJI | 1985/12/12 | 23 | MALE | 1111111222222 | 2008/12/11 | 12:00 | OUTPATIENT | UPPER |
| ○ | ○ | ○ | | 01236 | FUJIO FUJI | 1985/12/12 | 23 | UNKNOWN | 1111111333322 | 2008/12/11 | 16:40 | HOSPITALIZED OUTPATIENT | UPPER |
| ○ | | | | 01237 | FUJIKO FUJI | 1985/12/12 | 23 | FEMALE | 1112345611111 | 2008/12/12 | 09:30 | OUTPATIENT | UPPER |
| ○ | | | | 01238 | MASAHARU FUJIYAMA | 1969/02/06 | 39 | MALE | 1111112345611 | 2008/12/12 | 12:50 | INPATIENT | UPPER |
| ○ | | | | 01239 | FUSHIMI FUJI | 1985/12/12 | 23 | FEMALE | 1111111143215 | 2008/12/14 | 10:30 | INPATIENT | BRONCHIAL |

— A

LOGIN NAME: AAA  [LOGOUT]

FIG. 5

FEB 9, 2009
F: INSPECTION ROOM ICON
DRAG AND DROP ANY FROM INSPECTION LIST TO ANY
INSPECTION ROOM TO MAKE SETTING

| INSPECTION ROOM 1 | INSPECTION ROOM 2 | INSPECTION ROOM 3 |
|---|---|---|
| 1 | 0 | 1 |
| ATTENDING x x x | ATTENDING x x x | ATTENDING x x x |
| DEVICE x x x | DEVICE x x x | DEVICE x x x |

INSPECTION ROOM 3

| | PATIENT NAME | INSPECTION CONTENTS |
|---|---|---|
| NUMBER OF PERSONS INSPECTED: 0 | x x x x x x | x x x x x x |
| NUMBER OF PARSONS UNINSPECTED: 1 | x x x x x x | x x x x x x |
| TOTAL NUMBER OF PERSONS INSPECTED AND TO BE INSPECTED | | |
| ATTENDING DOCTOR | x x x x x x | |
| INSPECTION DEVICE | x x x x x x | |

CLOSE

| VISIT | ACCEPT | INSPECT | BILL | PATIENT ID | NAME | BIRTH DATE | AGE | SEX | ORDER NUMBER | SCHEDULED DATE | SCHEDULED TIME | INPATIENT/ OUTPATIENT DISTINCTION | INSPECTION ITEM |
|---|---|---|---|---|---|---|---|---|---|---|---|---|---|
| o | o | o | | 01234 | FUJISUKE FUJI | 1977/11/11 | 31 | MALE | 11111122222 | 2008/12/11 | 11:30 | INPATIENT | UPPER |
| o | o | | | 01235 | FUJIO FUJI | 1985/12/12 | 23 | MALE | 11111122222 | 2008/12/11 | 12:00 | OUTPATIENT HOSPITALIZED | UPPER |
| | | | | 01236 | FUJIO FUJI | 1985/12/12 | 23 | UNKNOWN | 1111111333322 | 2008/12/11 | 16:40 | OUTPATIENT | UPPER |
| | | | | 01237 | FUJIKO FUJI | 1985/12/12 | 23 | FEMALE | 1112345611111 | 2008/12/12 | 09:30 | OUTPATIENT | UPPER |
| | | | | 01238 | MASAHARU FUJIYAMA | 1969/02/06 | 39 | MALE | 1111112345611 | 2008/12/12 | 12:50 | INPATIENT | UPPER |
| | | | | 01239 | FUSHIMI FUJI | 1985/12/12 | 23 | FEMALE | 11111114321 5 | 2008/12/14 | 10:30 | INPATIENT | BRONCHIAL |

| FEB 9, 2009 DRAG AND DROP ANY FROM INSPECTION LIST TO ANY INSPECTION ROOM TO MAKE SETTING | | | | INSPECTION ROOM 3 | | | PATIENT NAME | INSPECTION CONTENTS |
|---|---|---|---|---|---|---|---|---|
| INSPECTION ROOM1 | INSPECTION ROOM2 | INSPECTION ROOM3 G | | NUMBER OF PERSONS INSPECTED | NUMBER OF PARSONS UNINSPECTED | | | |
| 1 | 0 | 0 | | 0 | 1 | | × × × × × × | × × × × × × |
| ATTEND-ING ××× | ATTEND-ING ××× | ATTEND-ING ××× | | ATTENDING × × × × × × | | | × × × | × × |
| DEVICE ××× | DEVICE ××× | DEVICE ××× | | DEVICE × × × × × × | | | | CLOSE |
| LIVE VIDEO IMAGE | LIVE VIDEO IMAGE | LIVE VIDEO IMAGE | | LIVE VIDEO IMAGE | | | | |

| VISIT | ACCEPT | INSPECT | BILL | PATIENT ID | NAME | BIRTH DATE | | SEX | TEL | RECEPTION DATE | RECEPTION TIME | INPATIENT/OUTPATIENT DISTINCTION | INSPECTION ITEM |
|---|---|---|---|---|---|---|---|---|---|---|---|---|---|
| ○ | ○ | ○ | ○ | 01234 | FUJISUKE FUJI | 1977/11/11 | 31 | MALE | 11111111122222 | 2008/12/11 | 11:30 | INPATIENT | UPPER |
| ○ | ○ | ○ | ○ | 01235 | FUJIO FUJI | 1985/12/12 | 23 | MALE | 11111111122222 | 2008/12/11 | 12:00 | OUTPATIENT HOSPITALIZED | UPPER |
| | | | | 01236 | FUJIO FUJI | 1985/12/12 | 23 | UNKNOWN | 11111111333322 | 2008/12/11 | 16:40 | OUTPATIENT | UPPER |
| | | | | 01237 | FUJIKO FUJI | 1985/12/12 | 23 | FEMALE | 1112345611111 | 2008/12/12 | 09:30 | OUTPATIENT | UPPER |
| | | | | 01238 | MASAHARU FUJIYAMA | 1969/02/06 | 39 | MALE | 1111112345611 | 2008/12/12 | 12:50 | INPATIENT | UPPER |
| | | | | 01239 | FUSHIMI FUJI | 1985/12/12 | 23 | FEMALE | 1111111143215 | 2008/12/14 | 10:30 | INPATIENT | BRONCHIAL |

LIVE VIDEO IMAGE

FIG. 10   F: INSPECTION ROOM ICON

FEB 9, 2009
DRAG AND DROP ANY FROM INSPECTION LIST TO ANY
INSPECTION ROOM TO MAKE SETTING

| INSPECTION ROOM 1 | INSPECTION ROOM 2 | INSPECTION ROOM 3 |
|---|---|---|
| 1 | 0 | 0 |
| ATTEND-ING xxx | ATTEND-ING xxx | ATTEND-ING xxx |
| DEVICE xxx | DEVICE xxx | DEVICE xxx |

ROOMS IN WHICH INSPECTION FOR SELECTED
ORDER CAN BE CONDUCTED ARE HIGHLIGHTED

INSPECTION ROOM 3

| | | | PATIENT NAME | INSPECTION CONTENTS |
|---|---|---|---|---|
| NUMBER OF PERSONS INSPECTED | 0 | NUMBER OF PARSONS UNINSPECTED | 1 | |
| TOTAL NUMBER OF PERSONS INSPECTED AND TO BE INSPECTED | | 1 | xxxxxx | xxxxxx |
| ATTENDING DOCTOR | xxxxxx | | xxxxxx | xxxxxx |
| INSPECTION DEVICE | xxxxxx | | | |

CLOSE

| VISIT | ACCEPT | INSPECT | BILL | PATIENT ID | NAME | BIRTH DATE | AGE | SEX | ORDER NUMBER | SCHEDULED DATE | SCHEDULED TIME | INPATIENT/ OUTPATIENT DISTINCTION | INSPECTION ITEM |
|---|---|---|---|---|---|---|---|---|---|---|---|---|---|
| ○ | ○ | ○ | ○ | 01234 | FUJISUKE FUJI | 1977/1/11 | 31 | MALE | 1111111122222 | 2008/12/11 | 11:30 | INPATIENT | UPPER |
| ○ | ○ | ○ | | 01235 | FUJIO FUJI | 1985/12/12 | 23 | MALE | 1111111122222 | 2008/12/11 | 12:00 | OUTPATIENT | UPPER |
| ○ | ○ | | | 01236 | FUJIO FUJI | 1985/12/12 | 23 | UNKNOWN | 1111111333322 | 2008/12/11 | 16:40 | HOSPITALIZED | UPPER |
| | | | | 01237 | FUJIKO FUJI | 1985/12/12 | 23 | FEMALE | 1112345611111 | 2008/12/12 | 09:30 | OUTPATIENT | UPPER |
| | | | | 01238 | MASAHARU FUJIYAMA | 1969/02/06 | 39 | MALE | 1111112345611 | 2008/12/12 | 12:50 | INPATIENT | UPPER |
| | | | | 01239 | FUSHIMI FUJI | 1985/12/12 | 23 | FEMALE | 1111111143215 | 2008/12/14 | 10:30 | INPATIENT | BRONCHIAL |

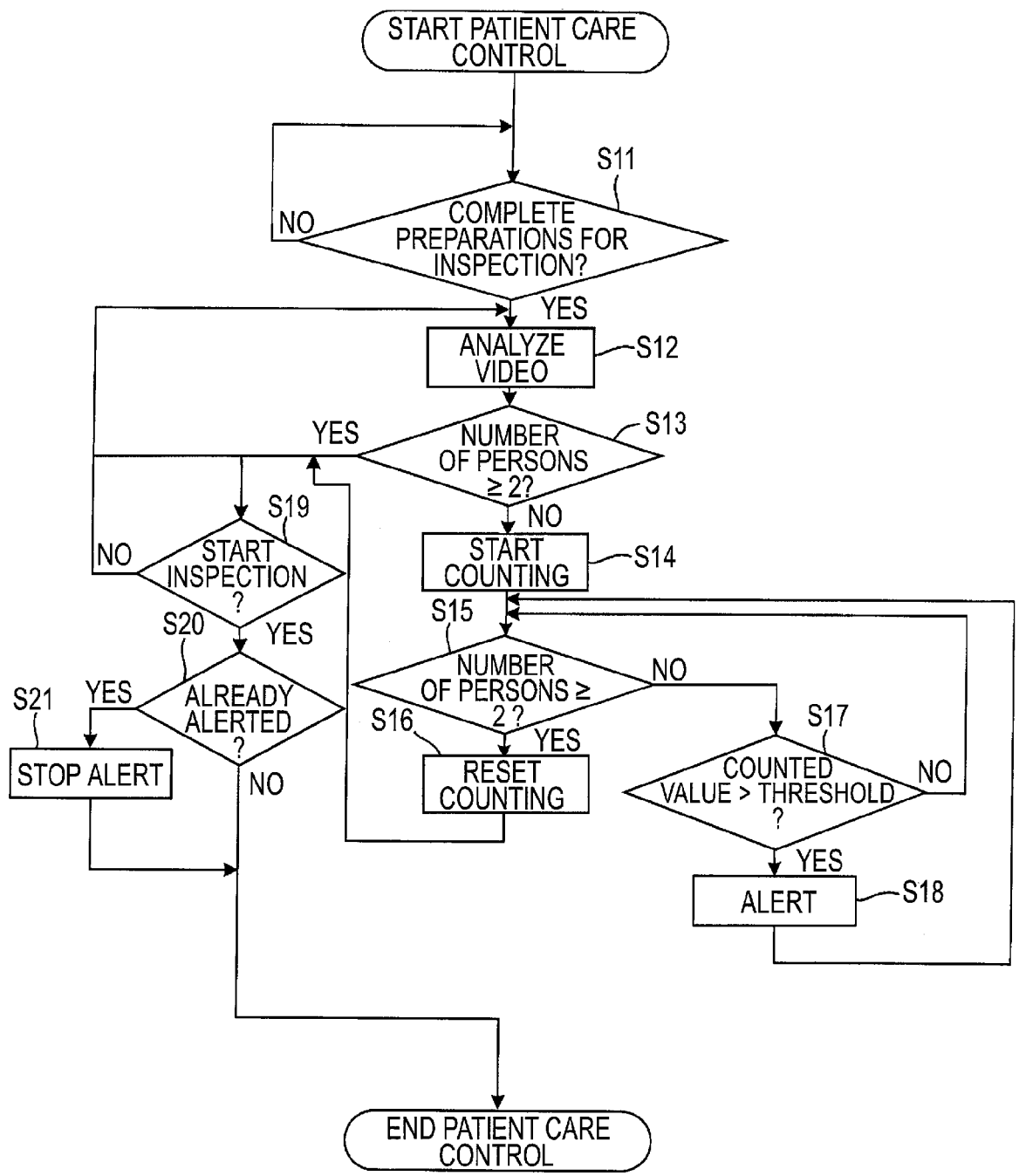

INSPECTION ROOM DECISION SUPPORT SYSTEM, INSPECTION ROOM DECISION SUPPORT METHOD AND COMPUTER READABLE MEDIUM

CROSS-REFERENCE TO RELATED APPLICATIONS

This application is based on and claims priority under 35 USC 119 from Japanese Patent Application Nos. 2009-228666 filed on Sep. 30, 2009 and 2010-195230 filed on Aug. 31, 2010; the entire contents of which are incorporated herein by reference.

BACKGROUND

1. Technical Field

The present invention relates to an inspection room decision support system, an inspection room decision support method, and a computer readable medium for supporting an inspection room allocation job (room allocation job) to decide one inspection room in which an inspection based on an endoscopic inspection order will be conducted, from a plurality of inspection rooms.

2. Related Art

There is proposed an inspection room decision support system for supporting a room allocation job to decide one inspection room in which an inspection based on a medical inspection order will be conducted, from plural inspection rooms. Patent Document 1 (JP-A-2005-044210) discloses a system in which an automatic acquisition pattern (in which use conditions of inspection kind of inspection instrument, region to be inspected, etc. have been determined) is stored in a reservation frame for each inspection room. To make a reservation, the system displays a reservation status of each inspection room. In response to an automatic reservation instruction issued, the system allocates a case waiting for inspection reservation to a reservation frame whose automatic acquisition pattern coincides with the contents of the case waiting for inspection reservation.

Allocation of reservation for an endoscopic inspection to an inspection room is required to be decided based on composite factors such as region to be inspected, kind of inspection device, etc. However, when such an allocation job is intended to be performed automatically as in the system disclosed in Patent Document 1, cost for constructing the system will increase.

SUMMARY

An illustrative aspect of the invention is to inexpensively provide a system, a method and a computer readable medium which can optimally allocate reservation for an inspection to an inspection room in an endoscopic inspection system.

[1] According to an aspect of the invention, an inspection room decision support system for providing support in deciding one inspection room in which a requested endoscopic inspection will be conducted, from a plurality of inspection rooms, the system includes: an input unit that inputs information; a registration unit that registers at least information about each of the inspection rooms, information about a number of persons waiting for inspection in each of the inspection rooms and information about an endoscope used in each of the inspection rooms into a database in accordance with the information inputted by the input unit; and a control unit which reads at least the information about each of the inspection rooms, the information about the number of persons waiting for inspection in each of the inspection rooms and the information about the endoscope in each of the inspection rooms from the database, and makes a display device display these pieces of information associated with each other.

[2] According to another aspect of the invention, an inspection room decision support method to be performed by a computer for providing support in deciding one inspection room in which a requested endoscopic inspection will be conducted, from a plurality of inspection rooms, the method includes: registering at least information about each of the inspection rooms, information about a number of persons waiting for inspection in each of the inspection rooms and information about an endoscope used in each of the inspection rooms into a database in accordance with the information inputted by an input unit; and controlling by reading at least the information about each of the inspection rooms, the information about the number of persons waiting for inspection in each of the inspection rooms and the information about the endoscope in each of the inspection rooms from the database, and making a display device display these pieces of information associated with each other.

[3] According to another aspect of the invention, a computer readable medium stores a program causing a computer to execute a process for the inspection room decision support method of [2].

With the configuration of any one of [1] to [3], it is possible to inexpensively provide a system, a method and computer readable medium which can optimally allocate reservation for an inspection to an inspection room in an endoscopic inspection system.

BRIEF DESCRIPTION OF THE DRAWINGS

FIG. 3 is a diagram showing a schematic configuration of each client PC in the endoscopic sector system shown in FIG. 2.

FIG. 4 is a view showing a basic screen of an application installed in the client PC shown in FIG. 2.

FIG. 5 is a view showing an example of a room allocation screen to which the basic screen shown in FIG. 4 is changed when an "allocate" button is pushed on the screen.

FIG. 7 is a view showing an example of a room allocation screen to which a basic screen of an application installed in a client PC shown in FIG. 6 is changed when an "allocate" button is pushed on the screen.

FIG. 9 is a view showing an example of a room allocation screen to which a basic screen of an application installed in a client PC shown in FIG. 8 is changed when an "allocate" button is pushed on the screen.

FIG. 10 is a view showing an example of a screen with highlighted room allocation icons.

FIG. 12 is a diagram showing an operation flowchart of patient care control performed in the system of the eighth modification.

DETAILED DESCRIPTION

An exemplary embodiment of the invention will be described below with reference to the drawings.

Figure 1:
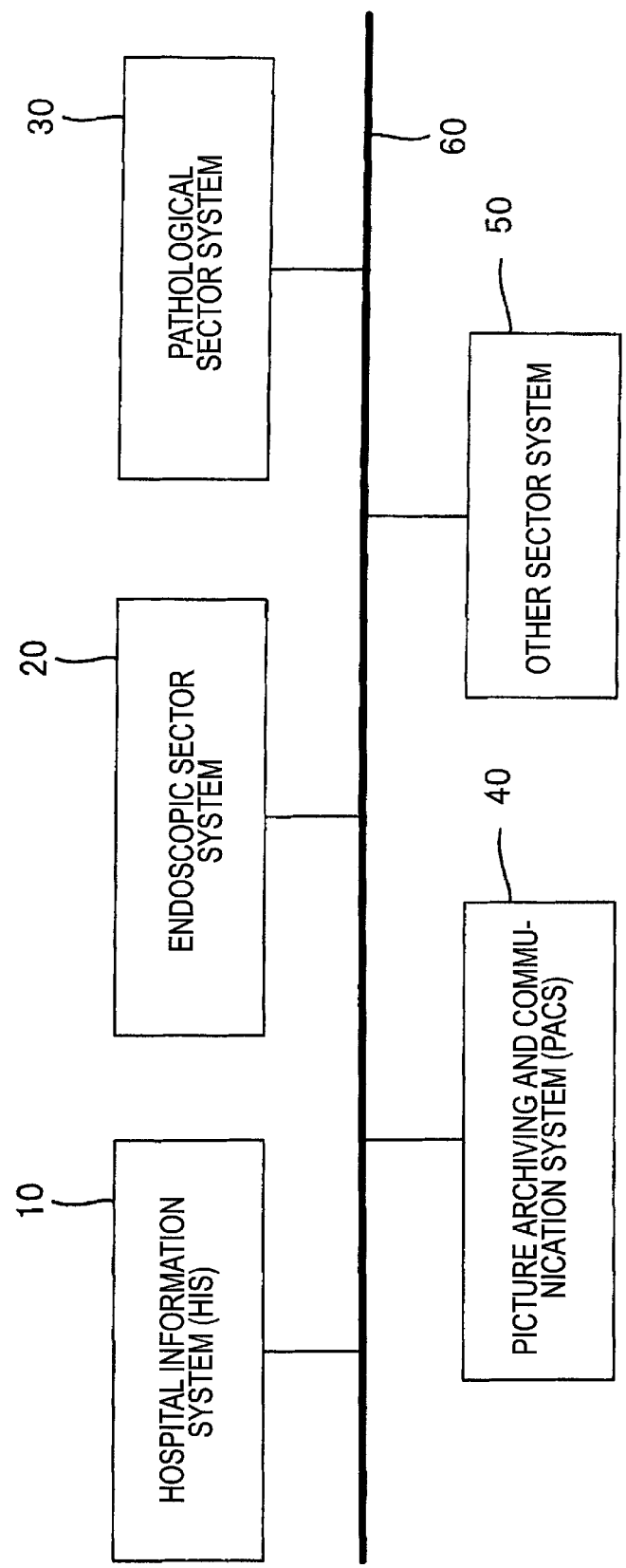
FIG. 1 is a diagram showing an overall configuration of a hospital system.

FIG. 1 is a view showing an overall configuration of a hospital system. The system shown in FIG. 1 includes a hospital information system (HIS) 10, an endoscopic sector system 20, a pathological sector system 30, a picture archiving and communication system (PACS) 40, and an other sector system 50. These systems 10 to 50 are connected to a hospital LAN 60 so that these systems 10 to 50 can work with one another.

The HIS 10 is a comprehensive system including a medical coding/billing system, a medical practice reservation system, a medical practice information system, etc. The HIS 10 has an electronic medical record database etc. Electronic medical records in which medical practice information of patients has been recorded are stored in the electronic medical record database.

Assume that an inspection request from another medical department is sent to the endoscopic sector. When information about the inspection request (order) (hereinafter referred to as inspection request information) in this case is issued, the inspection request information is transmitted to the endoscopic sector system 20 through the HIS 10.

For example, the inspection request information includes patient's information, order key information ("order number", "date and time of occurrence", etc.), request source information ("requesting department name", "requesting doctor name", "request date", etc.), order information ("requested disease name", "inspection purpose", "inspection kind", "inspection item", "inspection region", "comment", etc.), inspection reservation information ("inspection date", "conduct time", etc.), etc. The patient's information is information about a patient, including "patient ID as patient-specific information", "patient name", "birth date", "age", "sex", "inpatient/outpatient distinction", etc.

The endoscopic sector system 20 is a system for administering the endoscopic sector.

The pathological sector system 30 is a system for administering a pathological sector.

The PACS 40 is a system for electronically storing, retrieving and analyzing each inspection image from a medical image diagnostic device such as an endoscopic inspection device, a CT or an MRI.

The other sector system 50 is a system for administering the other sectors.

Figure 2:
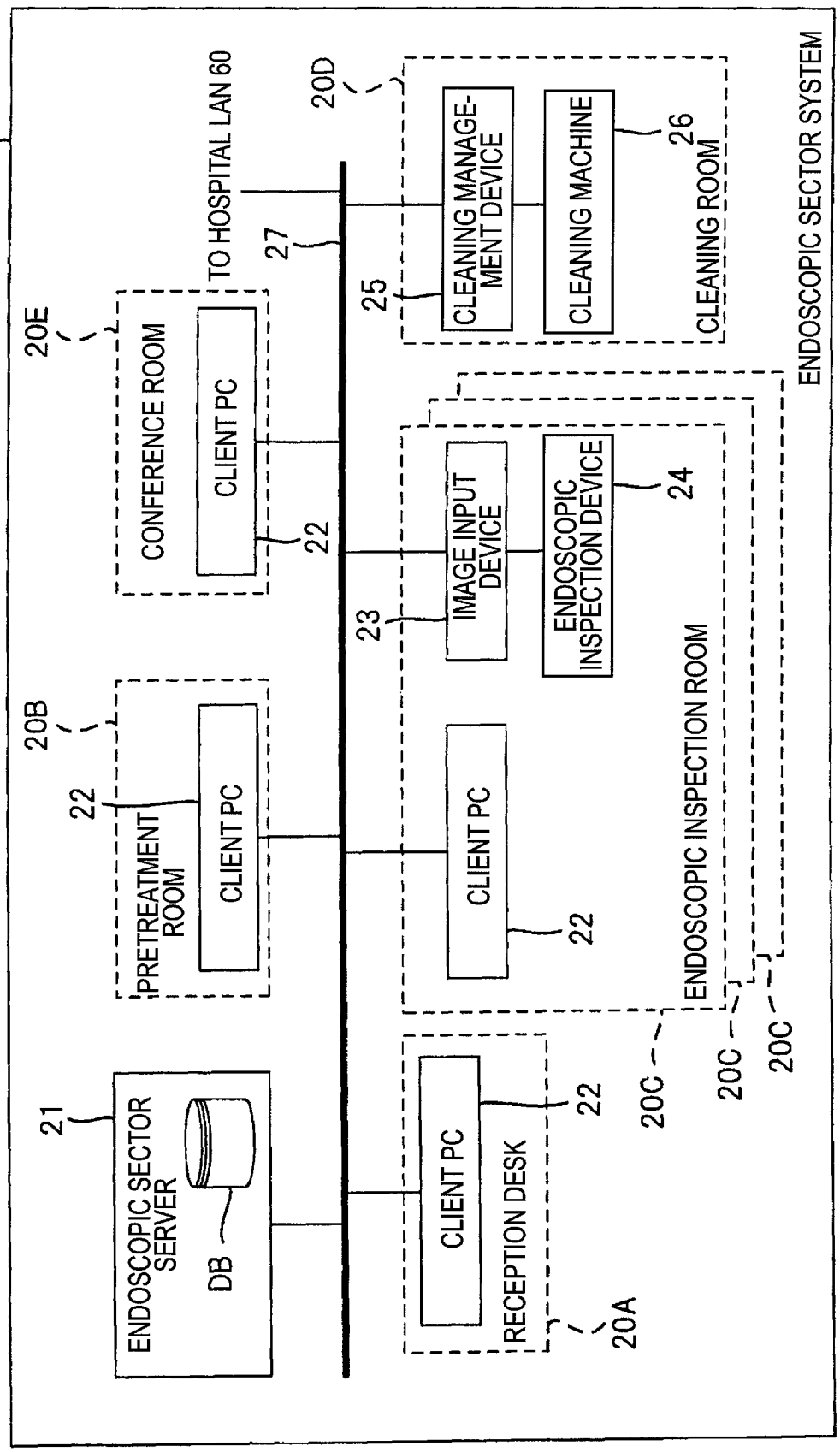
FIG. 2 is a diagram showing a schematic configuration of an endoscopic sector system in the system shown in FIG. 1.

FIG. 2 is a view showing a schematic configuration of an example of the endoscopic sector system in the system shown in FIG. 1. The endoscopic sector includes a reception desk 20A, a pretreatment room 20B, endoscopic inspection rooms (hereinafter referred to as inspection rooms simply) 20C, a cleaning room 20D, and a conference room 20E.

The reception desk 20A is a site for accepting inspections. The pretreatment room 20B is a room for interview and pretreatment before each endoscopic inspection. The inspection rooms 20C are rooms for endoscopic inspections. The cleaning room 20D is a room for cleaning endoscopes etc. used for the endoscopic inspections.

The endoscopic sector system 20 shown in FIG. 2 has an endoscopic sector server 21, client PCs 22, image input devices 23, endoscopic inspection devices 24, a cleaning management device 25 and a cleaning machine 26. The endoscopic sector server 21, the client PCs 22, the image input devices 23, and the cleaning management device 25 are connected to an intrasectoral LAN 27. The intrasectoral LAN 27 is connected to the hospital LAN 60.

FIG. 3 is a block diagram showing an internal configuration of each client PC in the endoscopic sector system shown in FIG. 2. As shown in FIG. 3, each client PC 22 includes an input portion 22a, a display portion 22b, a recording portion 22c, a transmission/reception portion 22d and a control portion 22e.

The input portion 22a is an input unit for performing various inputs. The input portion 22a is constituted by input devices such as a keyboard and a touch panel, and pointing devices such as a mouse and a trackball.

The display portion 22b is a display device for performing various displays such as an image and a report. The display portion 22b is constituted by an LCD, a CRT, or the like.

The recording portion 22c is constituted by a hard disk or the like for recording various data.

The transmission/reception portion 22d is constituted by a transmission/reception interface circuit or the like to execute processing for transmitting/receiving various instructions, various requests and various data through the intrasectoral LAN 27.

The control portion 22e includes a processor such as a CPU (Central Processing Unit), a program memory portion such as an ROM (Read-Only Memory) for storing programs, and a storage portion.

The storage portion in the control portion 22e is constituted by a system memory, a nonvolatile RAM (Random Access Memory) or the like, which forms work areas for executing the programs.

The control portion 22e performs control on the respective portions of the client PC 22 in accordance with the programs, various requests transmitted from the outside through the intrasectoral LAN 27, instruction information inputted from the input portion 22a, etc.

The image input devices 23 and the endoscopic inspection devices 24 are placed in the inspection rooms 20C respectively.

Each image input device 23 is connected to the endoscopic inspection device 24 in the inspection room 20C where the image input device 23 is placed. The image input device 23 is a device by which image data obtained by capturing images with the endoscopic inspection device 24 connected thereto is supplied to the endoscopic sector server 21. The image data supplied by the image input device 23 is archived by the PACS 40 under the control of the endoscopic sector server 21. Alternatively, an endoscopic inspection device integrated with the image input device 23 may be used as the endoscopic inspection device 24.

The cleaning machine 26 and the cleaning management device 25 are placed in the cleaning room 20D. The cleaning machine 26 is a device for cleaning endoscopes etc. used for endoscopic inspections.

The cleaning management device 25 is a computer which is connected to the cleaning machine 26 and by which information of a cleaning history or the like of the cleaning machine 26 is registered in the endoscopic sector server 21.

The endoscopic sector server 21 is a computer for generally controlling the client PCs 22, the image input devices 23, and the cleaning management device 25. A database DB is built in the endoscopic sector server 21. Various kinds of information (inspection request information, inspection result information etc.) are stored in the database DB.

A predetermined application program is installed in each client PC 22. By the program, the client PC 22 can refer to and edit data recorded in the database DB and register data in the database DB.

For example, a basic screen of this application is shown in FIG. 4. When a user starts up the application in the client PC 22 and logs into the application, the control portion 22e acquires basic screen data from the database DB and makes the display portion 22b display the basic screen shown in FIG.

4. The basic screen is constituted by a region A for displaying a list of inspection request information (partially extracted information), a region B for displaying various operation buttons, and a region C for displaying launchers available for the inspection request information selected on the list.

Processing items including "visit", "accept", "inspect", "bill", etc. are displayed in the list of the region A. When the processing indicated by each processing item is completed, the mark "◯" is displayed for the processing item. Data for displaying the mark is registered in the database DB by the endoscopic sector server 21 as soon as each processing is completed. When, for example, inspection is completed based on inspection request information, the endoscopic sector server 21 registers information, which indicates the completion of the inspection, into the database DB in association with the inspection request information. In this manner, the mark "◯" is displayed in the processing item "inspect". The information indicating whether each processing has been completed or not may be inputted manually, or may be automatically notified by the client PC 22 or the endoscopic inspection device 24.

The control portion 22*e* of the client PC 22 acquires data for displaying this basic screen from the database DB periodically, and makes the display portion 22*b* display the data.

This application has an "allocate" button B1 as an operation button. The "allocate" button B1 is displayed in the region B of the basic screen shown in FIG. 4. This button B1 is a button for performing a room allocation job to decide one inspection room in which a reserved inspection will be conducted, from a plurality of inspection rooms 20C.

When the "allocate" button B1 is pressed, the control portion 22*e* of the client PC 22 acquires data for display of a screen shown in FIG. 5 from the database DB, and makes the display portion 22*b* display the screen shown in FIG. 5. In the screen shown in FIG. 5, a room allocation screen is displayed in the location where the region B and the region C had been displayed till then.

The room allocation screen includes a region D for displaying inspection room icons F corresponding to inspection rooms 20C respectively and a region E for displaying details of an inspection room 20C corresponding to a selected inspection room icon F. When a user selects one from the inspection room icons F by use of the input portion 22*a*, detailed information of the selected inspection room icon F is displayed in the region E (FIG. 5 shows a state in which an icon of an inspection room 3 has been selected).

Name of an inspection room 20C, information about an inspection of the inspection room 20C (information about the number of persons inspected and the number of persons uninspected), information about an attending doctor conducting the inspection in the inspection room 20C (doctor name etc.), and information about an endoscopic inspection device 24 placed in the inspection room 20C (kind, maker, model No., etc.) are displayed in each inspection room icon F.

When a piece of inspection request information selected from a list of pieces of inspection request information displayed in the region A by use of the input portion 22*a* is dragged and dropped on a desired inspection room icon F in the screen (that is, the desired inspection room icon F is selected), an inspection based on the selected piece of inspection request information can be allocated to an inspection room corresponding to the desired inspection room icon F.

When the piece of inspection request information has been dragged and dropped on the desired inspection room icon F, the control portion 22*e* of the client PC 22 updates information about the inspection of the inspection room corresponding to the desired inspection room icon F, which information has been registered in the database DB (specifically, the number of persons uninspected is added by 1). The control portion 22*e* of the client PC 22 reads the information after updating again and updates the information about the inspection to be displayed in the inspection room icon F (the number of persons uninspected is added by 1).

When the piece of inspection request information is dragged and dropped on the desired inspection room icon F, it is preferable that the piece of inspection request information is to be recognized quickly as the piece of the inspection request information having been allocated to the inspection room. For example, the control portion 22*e* of the client PC 22 may add a mark indicating the piece of inspection request information has been allocated to the inspection room to the piece of inspection request information while storing information about the allocated inspection room in the database DB to be associated with the piece of inspection request information. The control portion 22*e* of the client PC 22 may delete the piece of inspection request information from the region A, while storing the information about the allocated inspection room in the database DB to be associated with the piece of inspection request information.

Information to be displayed in each inspection room icon F except the information about inspection is registered in the database DB by a user in advance. This registration is made, for example, by operating the input portion 22*a* of the client PC 22 based on a function of the application program installed in the client PC 22. Since information inputted through the input portion 22*a* is registered in the database DB through the transmission/reception portion 22*d* by the control portion 22*e*, the control portion 22*e* serves as a registration unit for registering the information inputted through the input portion 22*a* into the database DB.

Incidentally, the information except the information about inspection may be registered by another computer than the client PC 22 or may be registered by the endoscopic sector server 21. When the information except the information about inspection is registered by another computer than the client PC 22 or by the endoscopic sector server 21, the other computer or the endoscopic sector server 21 serves as a registration unit for registering the information into the database.

When the "allocate" button B1 is pushed down, the control portion 22*e* of the client PC 22 accesses the database DB to read information about an inspection of each inspection room 20C, information about a doctor (doctor name, etc.) and information about an endoscopic inspection device 24 from the database DB, and makes the display portion 22*b* display the screen of FIG. 5 including inspection room icons F displayed in association with these pieces of information.

With the aforementioned configuration, for example, information about an attending doctor conducting an inspection in each inspection room 20C and information about an endoscopic inspection device 24 placed in the inspection room 20C are displayed together with information about the inspection of the inspection room 20C on the display portion 22*b* of the client PC 22 in the reception desk. Therefore, an inspection room optimal for a reserved inspection can be decided based on comprehensive judgment of these pieces of information. As a result, both acceptance efficiency and inspection efficiency in medical treatment of an endoscopic inspection can be improved.

An available endoscopic inspection device differs from one region to be inspected to another. Accordingly, when at least information about the inspection and information about the inspection device are displayed in accordance with each inspection room, an inspection room optimal for a reserved inspection can be decided. In addition, time required for the inspection also differs from one doctor to another due to congeniality between the doctor and the inspection device and experience of the doctor with the inspection device. Accordingly, when information about the doctor is also displayed in accordance with each inspection room, more efficient allocation can be made.

Of the information about the inspection device and the information about the doctor, the information about the doctor does not have to be displayed. Although information about the number of persons inspected is also included as the information about inspection in the example of FIG. 5, it will go well as long as at least information about the total number of uninspected persons whose reservations have been allocated but who have not been inspected is included as the information about inspection.

In addition, information displayed in the region A may be restricted in the screen of FIG. 5.

For example, the control portion 22e may make the display portion 22b display only pieces of the inspection request information of the patients excepting the patients who have finished the inspections in the region A of the screen shown in FIG. 5. Specifically, when the "allocate" button B1 is pressed in the screen shown in FIG. 4, the control portion 22e makes the display portion 22b display only pieces of the inspection request information excepting pieces of the inspection request information of the patients which have finished the inspections (i.e., excepting the pieces of the inspection request information on the first line and the second line in the region A shown FIG. 5) from the list of pieces of the inspection request information in the region A shown in FIG. 5.

This restriction makes it possible to display only the information of the patient expected to have the inspection in the region A, which improves efficiency of the room allocation job.

Further, the control portion 22e may make the display portion 22b display only piece(s) of the inspection request information selected on the screen shown in FIG. 4 on the screen shown in FIG. 5. Specifically, when the "allocate" button B1 is pressed on the screen of FIG. 4 with one or more pieces of the inspection requesting information being selected in the region A, the control portion 22e makes the display portion 22b display only the selected one or more pieces of the inspection requesting information in the region A shown in FIG. 5.

This restriction makes it possible to display only the information of the patient expected to be allocated in the region A, which improves efficiency of the room allocation job.

If the information displayed in the region A is restricted, the inspection request information may be classified and displayed in accordance with each of the inspection items and each of the scheduled times. This further improves efficiency of the room allocation job.

In addition, in the screen shown in FIG. 5, the control portion 22e may make the display portion 22b highlight an inspection room icon F corresponding to the inspection room 20C to show it is under inspection.

A modification of the endoscopic sector system in the system shown in FIG. 1 will be described below.

<First Modification>

Figure 6:
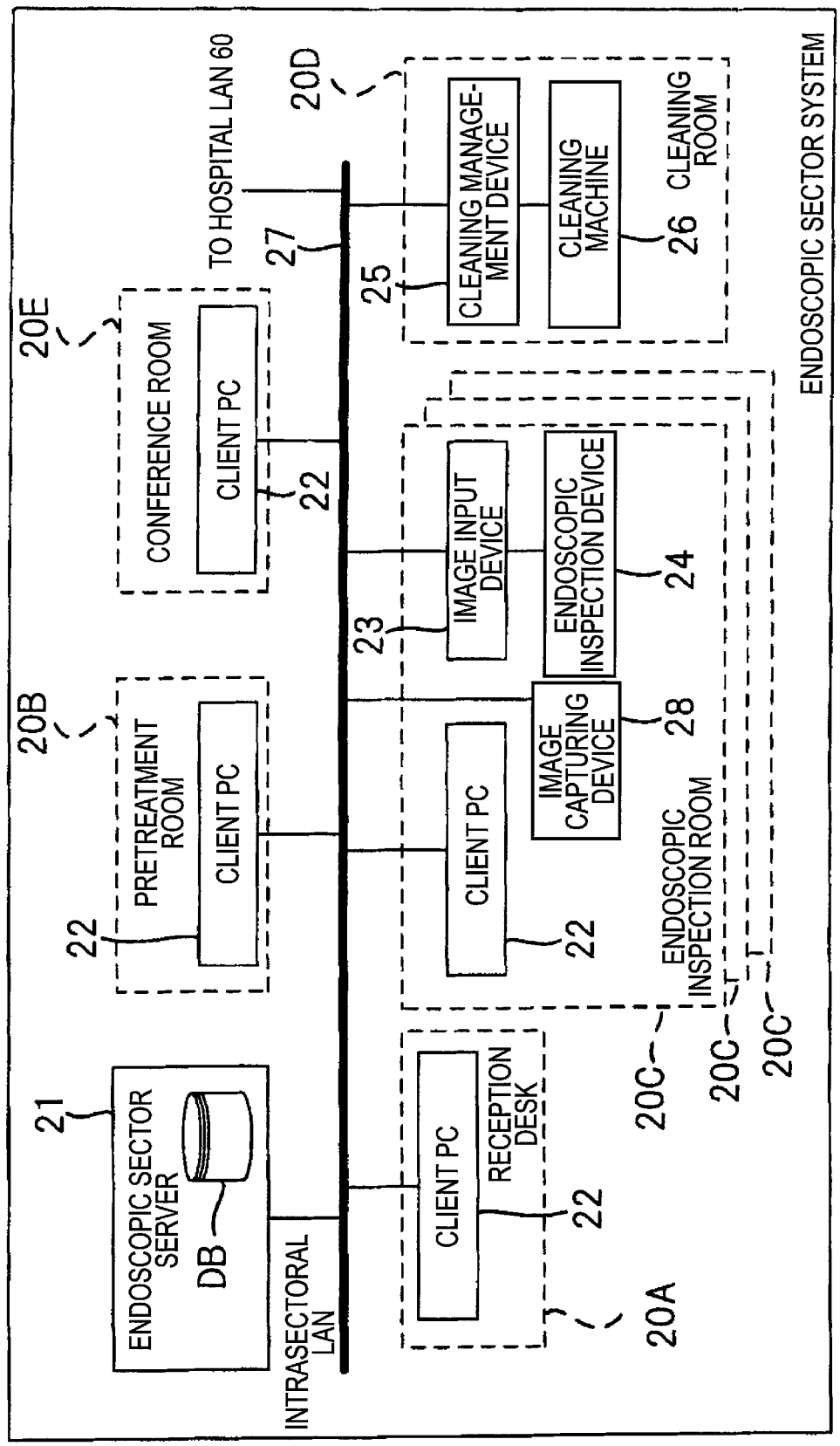
FIG. 6 is a view showing a first modification of the configuration of the system shown in FIG. 2.

FIG. 6 is a diagram showing a first modification of the endoscopic sector system in the system shown in FIG. 1. The system shown in FIG. 6 is different from the system in FIG. 2, in the point that an image capturing device 28 is added in each inspection room 20C.

The image capturing device 28 is a network camera connected to the intrasectoral LAN 27. The image capturing device 28 is controlled by the endoscopic sector server 21. The image capturing device 28 captures an image of the inside of the inspection room 20C where the image capturing device 28 is placed, and transmits data of the thus captured image to the endoscopic sector server 21.

A table in which serial numbers of the image capturing devices 28 are associated with the names of the inspection rooms 20C having the image capturing devices 28 placed therein respectively is registered in the database DB. The endoscopic sector server 21 reads the name of each inspection room 20C having an image capturing device 28 placed therein from the database DB based on the serial number of the image capturing device 28 as a sender of captured image data and the table.

The endoscopic sector server 21 records the received captured image data and information about the name of the inspection room 20C having the image capturing device 28 placed therein as a sender of the captured image data, on the database DB (which may be a storage portion exclusive for the captured image data) in association with each other.

Figure 7:
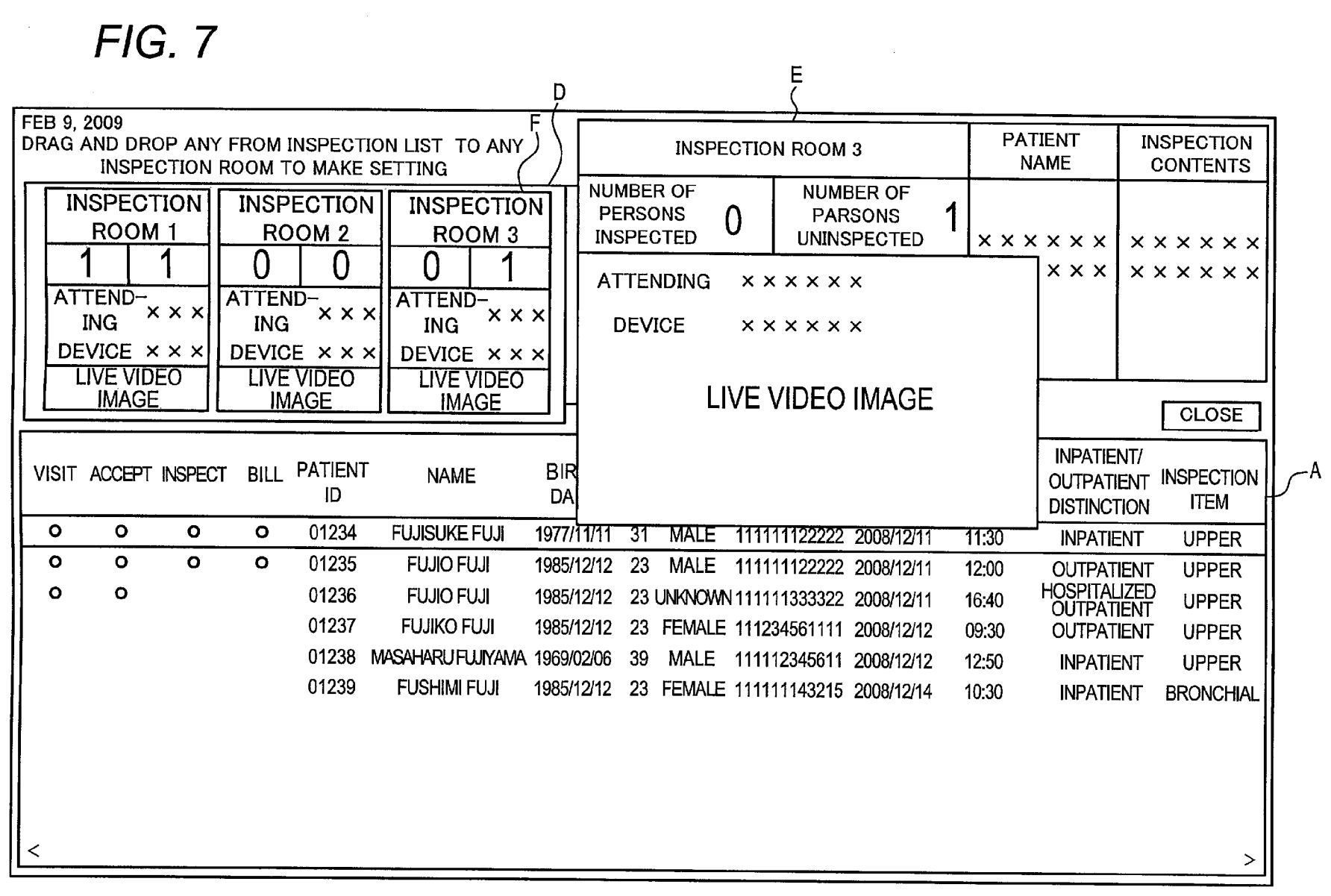

In a room allocation screen displayed in response to the "allocate" button B1 pushed down, the control portion 22e of the client PC 22 in the modification performs control to also display images (live video images) based on the captured image data recorded on the database DB, in association with the inspection room icons F (see FIG. 7). Specifically, the control portion 22e of the client PC 22 reads, from the database DB, captured image data corresponding to the names of the inspection rooms 20C to be displayed in accordance with the inspection room icons F, and performs control to display the captured image data in association with the inspection room icons F respectively.

As shown in FIG. 7, the live video images based on the captured image data captured by the image capturing devices 28 of the inspection rooms 20C are displayed in the inspection room icons F respectively, as well as information about the names of the inspection rooms 20C, information about inspections of the inspection rooms 20C, information about attending doctors of the inspection rooms 20C, and information about inspection devices of the inspection room 20Cs.

With such a configuration, a user can see the live video images displayed on the display portion 22b of the client PC 22 so as to grasp the state inside each inspection room 20C easily. When, for example, the user wants to contact a doctor regarding contents of an inspection, the user can instantly know whether the doctor can talk now or not or which inspection room the doctor is in, so that the user can communicate with the doctor smoothly. As a result, an inspection request can be allocated to an inspection room efficiently.

A live video image of a selected inspection room may be displayed in an enlarged mode in the region E as shown in FIG. 7. In this manner, the situation of the inspection room can be checked easily. In addition, the live video images do not have to be displayed in the respective inspection room icons F in the region D shown in FIG. 7 but a live video image of a selected inspection room may be displayed in the region E only when the inspection room icon F has been selected.

Although this modification has been described in the case where the image capturing device 28 is provided in each of the inspection rooms 20C, image capturing devices 28 may be provided only in part of the inspection rooms 20C. In this case, images based on captured image data may be displayed only in inspection room icons F corresponding to the inspection rooms 20C in which the image capturing devices 28 are placed.

<Second Modification>

Figure 8:
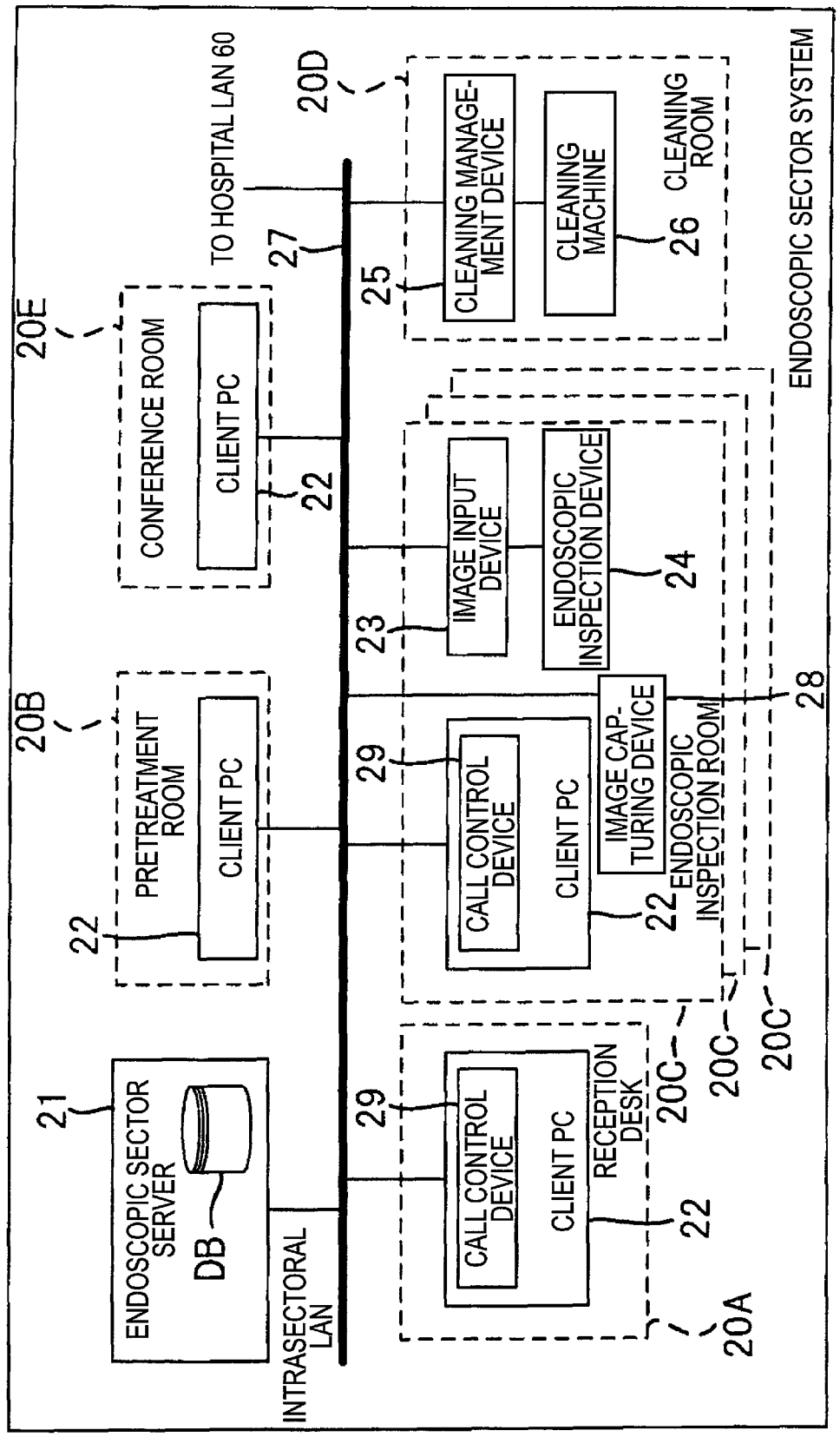
FIG. 8 is a diagram showing a second modification of the configuration of the system shown in FIG. 2.

FIG. 8 is a diagram showing a second modification of the endoscopic sector system in the system shown in FIG. 1. The system shown in FIG. 8 is different from the system shown in FIG. 6, in the point that a call control device 29 is added to each of client PCs 22 in the inspection rooms 20C and the reception desk 20A.

The call control device 29 includes the control portion 22*e* and a microphone and a speaker connected to the control portion 22*e*. A call using the microphone and the speaker can be made between two call control devices 29 under the control of the control portions 22*e*.

When the "allocate" button B1 is pushed down in the basic screen shown in FIG. 4, the control portion 22*e* of the client PC 22 makes the display portion 22*b* display a screen shown in FIG. 9. The screen shown in FIG. 9 is different from the screen shown in FIG. 7, in the point that a call icon G for issuing an instruction to make a call to a person in an inspection room corresponding to each inspection room icon F is displayed in the inspection room icon F.

When, for example, the call icon G of the inspection room 3 is clicked by a user operating the client PC 22 in the reception desk 20A, the control portion 22*e* of the client PC 22 in the reception desk 20A communicates with the call control device 29 of the inspection room 3 to validate connection to the call control device 29 of the inspection room 3 to thereby perform control to enable a call with the call control device 29 of the inspection room 3. In this manner, a call can be made between a person in the reception desk 20A and a person in the inspection room 3.

With this configuration, when, for example, a user wants to contact a doctor regarding contents of an inspection, the user can call the doctor after the user confirms whether the doctor can talk now or not or which inspection room the doctor is in, based on live video images. Thus, the user can communicate with the doctor smoothly. As a result, a job for allocating an inspection room can be performed efficiently.

Call control devices 29 may be mounted in client PCs in other rooms such as the pretreatment room 20B, the endoscopic inspection rooms 20C and the conference room 20E, besides the reception desk 20A. Instead of displaying the call icon G, a menu "call" may be displayed when an inspection room icon F is, for example, right-clicked. When the menu is selected, a call can be made. In addition, the configuration for displaying the menu "call" and enabling a call may be combined with the system shown in FIG. 2. In addition, configuration may be made so that call control devices 29 are mounted only in part of the client PCs 22 of all the endoscopic inspection rooms 20C.

<Third Modification>

This modification is configured in such a manner that information about regions (upper, lower, bronchial, etc.) each endoscopic inspection device 24 can inspect can be also registered as information about the endoscopic inspection device 24 in the database DB in one of the system configurations shown in FIGS. 2, 6 and 8.

The control portion 22*e* of each client PC 22 in the modification serves as a specification unit which specifies inspection rooms in each of which an inspection based on inspection request information can be conducted, based on contents of the inspection and the information about the endoscopic inspection devices 24, and as a notification unit which makes the display portion 22*b* display information so as to notify the outside of the inspection rooms specified by the specification unit.

When, for example, one piece is selected from the pieces of inspection request information on the room allocation screen shown in FIG. 5, the control portion 22*e* of the client PC 22 specifies inspection rooms 20C in each of which an inspection item included in the selected piece of inspection request information can be conducted, based on the inspection item and information about the endoscopic inspection devices 24 of the inspection rooms 20C which information has been acquired for display of the inspection room icons F. Then, in order to notify a user of the specified inspection rooms 20C (for example, assume they are inspection rooms 5 and 6), the client PC 22 highlights and displays the inspection room icons F corresponding to the specified inspection rooms, for example, as shown in FIG. 10.

With this configuration, a user can instantly know inspection rooms in each of which an inspection based on one piece of inspection request information can be conducted, by simply selecting the piece of inspection request information on the room allocation screen shown in FIG. 5. Accordingly, the user can select an optimal inspection room from the inspection rooms in each of which the inspection can be conducted, in consideration of congestion states, doctor skills, etc. so that the user can decide an inspection room more promptly.

Any method can be used in place of the highlight display method as long as the display method can distinguish the inspection rooms in each of which the inspection based on the selected piece of inspection request information can be conducted. For example, in which inspection rooms the inspection can be conducted may be displayed by words in a pop-up display manner. Alternatively, the inspection rooms in each of which the inspection can be conducted may be specified by the endoscopic sector server 21.

<Fourth Modification>

This modification is configured in such a manner that information (a medicine name list) etc. about medicines which are prepared in each inspection room can be registered in the database DB in association with the name of the inspection room 20C by the client PC of the inspection room and the information about medicines can be also displayed on a room allocation screen in any one of the system configurations shown in FIGS. 2, 6 and 8.

In the room allocation screen displayed in response to the "allocate" button B1 pushed down as shown in FIG. 5 or the like, the control portion 22*e* of the client PC 22 in this modification performs control to also display the medicine information recorded on the database DB in association with the inspection room icons F. Specifically, the control portion 22*e* of the client PC 22 reads, from the database DB, the medicine information corresponding to the names of the inspection rooms 20C to be displayed in the inspection room icons F respectively, and performs control to display the medicine information in association with the inspection room icons F.

Necessary medicines vary according to contents of inspections. With this configuration, room allocation can be made also in consideration of the medicine information so that more efficient room allocation can be achieved.

The medicine information may be registered by another computer than the client PC 22 or by the endoscopic sector server 21.

<Fifth Modification>

This modification is configured in such a manner that information about job progress status (status information such as inspecting, cleaning endoscopes, preparing medicines, and waiting for inspection) in each inspection room can be registered in association with the name of the inspection room 20C by the client PC of the inspection room 20C and the information about job progress status can be also displayed in a room allocation screen in any one of the system configurations shown in FIGS. 2, 6 and 8.

In the room allocation screen displayed in response to the "allocate" button B1 pushed down as shown in FIG. 5 or the like, the control portion 22*e* of the client PC 22 in this modification performs control to also display the progress status information recorded on the database DB in association with the inspection room icons F. Specifically, the control portion 22e of the client PC 22 reads, from the database DB, the progress status information corresponding to the names of the inspection rooms 20C to be displayed in the inspection room icons F respectively, and performs control to display the progress status information in association with the inspection room icons F.

The progress status information may be inputted manually by use of the input portion 22a of the client PC 22. Each endoscopic inspection device 24 may have a function capable of automatically creating information of progress status of an inspection.

For example, the endoscopic inspection device 24 may be designed to have a function of detecting whether an endoscope is connected or not. When connection of the endoscope is detected, the endoscopic inspection device 24 registers information indicating that an endoscopic inspection is being conducted into the database DB of the endoscopic sector server 21. When connection of the endoscope is not detected, the endoscopic inspection device 24 registers information indicating an inspection waiting state or an endoscope cleaning state into the database DB. The control portion 22e of the client PC 22 may acquire information about job progress status in each inspection room 20C based on the registered information so that the information about job progress status can be displayed in the room allocation screen.

When there are a plurality of inspection rooms having no person waiting for inspection, it is efficient to select an inspection room in which inspection can be conducted soon. With this configuration, the progress status in each inspection room is also displayed. Accordingly, it is possible to grasp an inspection room in which inspection can be conducted soon, so that it is possible to achieve efficient room allocation.

The progress status information may be registered by another computer than the client PC 22 or by the endoscopic sector server 21.

<Sixth Modification>

This modification is configured in such a manner that inspection image data obtained by each endoscopic inspection device 24 in a period from an inspection start (image capturing start) to an inspection end (image capturing end) and captured image data captured by each image capturing device 28 in the period from the inspection start to the inspection end can be recorded in association with each other in the system configuration shown in FIG. 6 or 8. According to this configuration, it is possible to use the captured image data also as evidence video when there was a medical accident etc.

<Seventh Modification>

Generally, the endoscopic inspection has the following procedures. Firstly, the doctor or nurse calls a patient to the inspection room. He/She turns the endoscope on for the inspection with the patient being laid on the inspection bed. Next, He/She completes the preparations of the endoscope by conducting operations required for the inspection such as attaching an endoscopic probe and setting various items. After the completion of the preparations, the display portion 22b of the client PC or a display portion of the endoscope displays captured images as a preview video being captured by the endoscope. And the endoscope becomes in a ready state until the capturing for the inspection starts. After the completion of the preparations, the doctor inserts the endoscopic probe into the body of the patient with viewing the preview video, which brings the end portion of the endoscope to the region to be inspected. And, after the end portion of the endoscope arrives at the region to be inspected, the doctor performs capturing for the inspection. After the doctor finished the capturing, the data of captured images is stored into the database DB through the image input device.

However, it often happens that in the actual medial practice, it takes much time until starting the inspection by the doctor after the completion of the preparations. The endoscopic inspection requires inserting the endoscope into the body of the patient. So, the endoscopic inspection inflicts physical pain and mental pain on the patient more than other inspections such as a mammographic inspection, a X-ray inspection and a blood test. That is, if the patient is waiting a long time even after called into the inspection room, the mental pain on the patient would be enormous. This seventh modification aims to relieve the mental pain of the patient as much as possible by employing a patient care control. In the patient care control, if the patent is waiting a long time, an alert is transmitted to a person looking at the client PC through the client PC.

The system of the seventh modification has the same configuration as the system shown in FIG. 2. However, in the system of the seventh modification, the endoscopic sector server 21 stores a program into an internal memory for performing the above patient care control. A CPU (Central Processing Unit) in the endoscopic sector sever 21 executes this program, which performs the patient care control.

Figure 11:
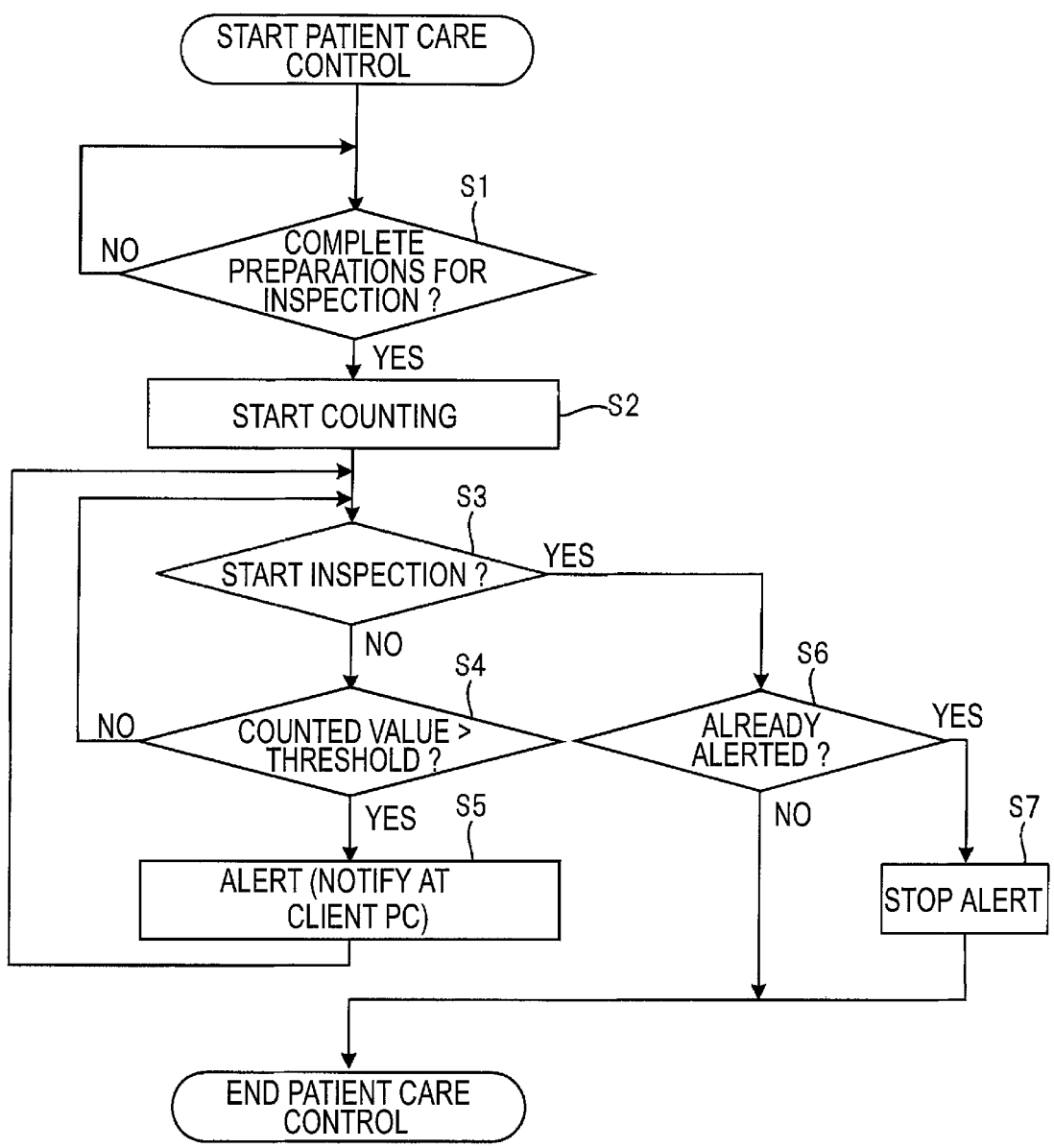
FIG. 11 is a diagram showing an operation flowchart of patient care control performed in the system of the seventh modification.

FIG. 11 is a diagram showing an operation flowchart of the patient care control performed in the system of the seventh modification of the endoscopic sector system 21 of the system shown in FIG. 1.

Firstly, the endoscopic sector server 21 determines if the preparations for the endoscopic inspection are completed in the inspection room 20C (Step S1). For example, when the preparations are completed by finishing the setting of the endoscope, the endoscope outputs the preview video. And, when the endoscopic sector server 21 receives the preview video through the image output device 23, the endscopic sector server 21 determines the preparations for the endoscopic inspection have been completed. However, when the endoscopic sector server 21 does not receive the preview video, the endoscopic sector server 21 determines the preparations for the endoscopic inspection have not been completed. Alternatively, the client PC in the inspection room 20C may be configured to transmit a notice manually issued by the doctor or nurse indicating the preparations for the endoscopic inspection are completed. In this case, the endoscopic sector server 21 determines the completion of the preparations for the endoscopic inspection on the basis of receiving input information based on the notice. The first frame of this preview video and the input information would be preparation completion information indicating the preparations for the endoscopic inspection have been completed, respectively.

If the endoscopic sector server 21 acquires the preparation completion information (Step S1: Yes), the endoscopic sector server 21 start counting of elapsed time from the time at which the endoscopic sector server 21 acquires the preparation completion information (Step S2).

Next, the endoscopic sector server 21 determines if the endoscopic inspection has started (Step S3). For example, the endoscopic sector server 21 determines the endoscopic inspection has started when the endoscopic sector server 21 receives the data of captured image firstly captured by the doctor. Alternatively, the client PC in the inspection room 20C may be configured to transmit a notice manually issued by the doctor or nurse indicating the endoscopic inspection has started. In this case, the endoscopic sector server 21 determines the start of the inspection on the basis of receiving input information based on the notice. The data of firstly captured image and the input information would be inspection start information indicating the endoscopic information has started, respectively. Hereinafter, the endoscopic sector server 21 is configured to determine the start of the inspection on the basis of receiving the data of firstly captured image.

When the endoscopic sector server 21 does not receive the inspection start information (Step S3: No), the endoscopic sector server 21 determines if the elapsed time from the time at which the endoscopic sector sever 21 acquires the preparation completion information exceeds the threshold. If the elapsed time exceeds the threshold (Step S4: Yes), the endoscopic sector server 21 performs the processing in Step S5. If the elapsed time does not exceed the threshold (Step S4: No), the endoscopic sector server 21 performs the processing of Step S3.

In Step S5, the endoscopic sector server 21 determines the patient is waiting a long time after the completion of the preparations for the endoscopic inspection, and the endoscopic sector server 21 performs alert processing to inform the doctor, nurse and another hospital staff of the patient being waiting.

Specifically, the endoscopic sector server 21 displays alert information indicating there is a waiting patient on the screen shown in FIG. 5, thereby alert a person who is opening the screen of FIG. 5. For example, the endoscopic sector server 21 highlights the inspection room icon F corresponding to the inspection room 20c of the waiting patient and displays string information describing "An patient is waiting for starting the inspection in this inspection room. Care for the patient promptly." The alert information is not limited to be displayed on the screen of FIG. 5, may be displayed on any one of the available screens of the client PCs. If displaying the alert information on the screen excepting the screen shown in FIG. 5, information about the inspection room 20C (i.e., room number, attending doctor, etc.,) and the above described string information may be displayed with being associated with each other. For example, the string information "An patient is waiting in the inspection room 3 (attending doctor: XXX). Care for the patient promptly" may be displayed so that the person could understand easier. Alert tone together with the string information may be emitted.

This make it possible for the person in front of the client PC to recognize the patient is waiting, instruct anyone to care for the patient by making a phone call to the inspection room and urge the doctor of the inspection room to accelerate the start of the inspection, which relieves the mental pain of the patient.

In the described step S3, the endoscopic sector server 21 regards the time of first capturing of the image as the inspection start. So, actual waiting time of the patient equals to a period obtained by subtracting a period between the endoscope insertion into the body of the patient and the start of first capturing of the image from a period between the completion of the preparations for the inspection and the inspection start. So, the threshold compared with the elapsed time in Step S4 is required to be determined considering a (average) period between the endoscope insertion into the body of the patient and the start of first capturing of the image.

For example, suppose that the system is configured to transmit an alert in a case where the patient is waiting more than ten minutes and the threshold compared with the elapsed time in Step S4 is set ten minutes. In this case, when it takes only five minutes from the endoscope insertion into the body of the patient to the start of first capturing of the image, the alter would be transmitted even if the patient is waiting actually five minutes.

The period between the endoscope insertion into the body of the patient and the start of first capturing of the image varies due to such as region to be inspected (Upper, Lower) and skill level of doctor. So, it is preferable that the threshold is set to vary in accordance with at least one of each of the regions to be inspected and each of the doctors.

In Step S3, if the endoscopic sector server 21 determines the inspection has started, the endoscopic sector server 21 determines if the endoscopic sector server has already transmitted the alert (Step S6). If the endoscopic sector server 21 has already transmitted the alert (Step S6: No), the endoscopic sector server 21 stops the alert (Step S7) to finish the patient care control. If the endscopic sector server 21 has not transmitted the alert yet (Step S6: No), the endoscopic sector server 21 ends the patient care control accordingly.

The patient care control can relieve the mental pain of the patient of the endoscopic inspection. As a result, unnecessary troubles with the patient may be prevented and a degree of patient's satisfaction for the hospital may be increased.

<Eighth Modification>

This modification explains an alternative method for the patient care control. Suppose that the system has the same configuration as that shown in FIG. 6. Also, as in the system of the seventh modification, the endoscopic sector server 21 stores the program for performing the patient care control in the internal memory thereof. The CPU (Central Processing Unit) of the endoscopic sector server 21 executes the program, which performs the patient care control.

FIG. 12 is a diagram showing an operation flowchart of the patient care control performed in the system of the eighth modification. The endoscopic sector server 21 performs the processing shown in FIG. 12 for each of the inspection rooms 20C.

Firstly, the endoscopic sector server 21 determines if the preparations of the endoscopic inspection are completed. (Step S11). This determination process is same as the process explained in the seventh modification.

If the endoscopic sector server 21 acquires the preparation completion information (Step S11: Yes), the endoscopic sector server 21 start analyzing a video transmitted from the image capturing device 28 installed in the inspection room 20C (Step S12). Specifically, the endoscopic sector server 21 detects the number of persons using a combination of the known face detection processing and the known motion detection processing, etc.

On the basis of the analyzing result, the endoscopic sector server 21 performs processing of Step S19 if the number of persons in the video is two or more (Step S13: Yes). The endoscopic sector server 21 performs processing of Step S14 if the number of persons in the video is less than two.

In Step S14, the endoscopic sector server 21 starts counting of elapsed time from the time point when the number of persons in the video is less than two. Next, if the number of persons in the video becomes two ore more (Step S15: Yes), the endoscopic sector server 21 resets counting of the elapsed time (Step S16) and performs the processing of Step S19. If the number of persons in the movie is kept less than two (Step S15: No), the endoscopic sector server 21 compares the counting of elapsed time with the threshold.

On the basis of the comparison result in Step S17, if the counting (elapsed time) exceeds the threshold, the endoscopic sector server 21 issues the alert in a similar way to the seventh modification. This is because it is determined that only a patient in the inspection room 20C is waiting a time exceeding the threshold after the completion of the preparations for the inspection.

On the basis of the comparison result in Step S17, if the counting (elapsed time) does not exceed the threshold, the endoscopic sector server 21 performs the processing of Step S15. After performing the processing of Step S18, the endoscopic sector server 21 also performs the processing of Step S15.

In the processing of Step s19 performed after "yes" of Step S13 or Step S16, the endoscopic sector server 21 determines if the endoscopic inspection has started in the inspection room 20C. The determination processing is the same as the processing explained in the seventh modification.

If the endoscopic sector section 21 determines the inspection has started in Step S19, the endoscopic sector server 21 determines if the endoscopic sector server 21 has already transmitted the alert. If the endoscopic sector server 21 has already transmitted the alert, the endscopic sector server stops the alert (Step S21) to finish the patient care control. If the endoscopic sector server 21 has not tranmitted the alert yet (Step S20), the endscopic sector server 21 finishes the patient care control accordingly.

The threshold compared with the counting in Step S14 may be set to such a tolerate value in which the patient is allowed to be waiting alone after the completion of the preparations for the inspection. The threshold is not required to be set for each of the doctors and each of the regions to be inspected.

The patient care control makes it possible to transmit a necessary alert for caring the patient when the period in which the patient is waiting alone after the completion of the inspection preparations exceeds the threshold. as the ases in which the patient is waiting after the completion of the inspection preparations, there is a case in which the patient is waiting even though the doctor or the nurse is in the inspection room 20C, and there is a case in which the patient is waiting alone in the inspection room 20C. The former case does not require the alert very much since the person who would care the patient is in the inspection room 20C. The latter case requires the alert very much since a feeling of anxiety of the patient would be increased. The patient care control shown in FIG. 12 can recognize only the latter case requiring the alert, which cuts waste and controls efficiency.

The patient care control shown in FIG. 11 may be incorporated into any one of the systems of the first to sixth modifications. The patient care control shown in FIG. 12 may be incorporated into any one of the systems of the second to sixth modifications.

As described above, the following matters are disclosed in the specification.

The disclosed inspection room decision support system for providing support in deciding one inspection room in which a requested endoscopic inspection will be conducted, from a plurality of inspection rooms, the system includes: an input unit that inputs information; a registration unit that registers at least information about each of the inspection rooms, information about a number of persons waiting for inspection in each of the inspection rooms and information about an endoscope used in each of the inspection rooms into a database in accordance with the information inputted by the input unit; and a control unit which reads at least the information about each of the inspection rooms, the information about the number of persons waiting for inspection in each of the inspection rooms and the information about the endoscope in each of the inspection rooms from the database, and makes a display device display these pieces of information associated with each other.

With this configuration, information about the number of persons waiting for inspection in each inspection room and information about an inspection device placed in the inspection room are displayed on the display device. Accordingly, an optimal inspection room for a requested inspection can be decided based on comprehensive judgment of these pieces of information. As a result, both acceptance efficiency and inspection efficiency in medical treatment of an endoscopic inspection can be improved.

In the disclosed inspection room decision support system, the registration unit may further register information about an attending doctor conducting inspection in each of the inspection rooms into the database. The control unit may read the information about the doctor for each of the inspection rooms from the database, and make the display device display the information about the doctor in association with each of the inspection rooms.

With this configuration, information about a doctor in each inspection room together with information about the number of persons waiting for inspection in the inspection room is also displayed on the display device. Accordingly, an optimal inspection room for a requested inspection can be decided based on comprehensive judgment of these pieces of information.

In the disclosed inspection room decision support system, the control unit may read a list of inspection request information about each of the requested inspections from the database, and make the display device display the list of the inspection request information together with the information about each of the inspection rooms. When (i) one piece of the inspection request information is selected through the input unit from the list of the inspection request information displayed on the display device, and (ii) one piece of the information about each of the inspection rooms is selected through the input unit from the information about each of the inspection rooms displayed on the display device, the registration unit may add one to the number of persons waiting for inspection in the selected inspection room and register the added number of persons into the database for updating.

With this configuration, such as the inspection request information, the information about each of the inspection rooms, the information about the number of persons waiting for inspection in each of the inspection rooms and the information about the endoscope in each of the inspection rooms can be confirmed. And only selecting pieces of the displayed inspection request information and pieces of the displayed information about each of the inspection rooms can determines optimally inspection rooms for the requested inspections.

In the disclosed inspection room decision support system, the control unit may make the display device display inspection request information excepting inspection request information about a completed inspection from the list of the inspection request information about each of the requested inspection.

With this configuration, the determination of the room allocation can be efficient because the display device displays only inspection request information of unconducted inspections each requiring the room allocation.

In the disclosed inspection room decision support system, from the display inspection request information about each of the requested inspection, the control unit may make the display device only display the one piece of the inspection request information selected through the input unit.

With this configuration, it is possible to prevent a mistake of the room allocation from occurring, which generates efficient medical practices because the display device only displays the selected inspection request information.

In the disclosed inspection room decision support system, when (i) one piece of the inspection request information is selected through the input unit from the list of the inspection request information displayed on the display device, and (ii) one piece of the information about each of the inspection rooms is selected through the input unit from the information about each of the inspection rooms displayed on the display device, the control unit may delete the selected one piece of the inspection request information from a screen of the display device.

With this configuration, it is possible to prevent reselect the selected inspection request information having been allocated to one of the inspection rooms, which prevents a mistake of the room allocation from occurring. As a result, this configuration generates efficient medical practices In the disclosed inspection room decision support system, the inspection room decision support system may further include: a captured image data acquisition unit that acquires data of captured images from image capturing devices placed in at least part of the inspection rooms respectively, the captured images being obtained by the image capturing devices which capture images of insides of the at least part of the inspection rooms where the image capturing devices are placed. The control unit makes the display device display the data of each captured image captured by a corresponding one of the image capturing devices in each or a selected one of the at least part of the inspection rooms, in association with the information about the inspection room.

With this configuration, a user can see captured images displayed on the display device so as to grasp the state inside each inspection room easily. When, for example, the user wants to contact a doctor regarding contents of an inspection, the user can instantly know whether the doctor can talk now or not or which inspection room the doctor is in, so that the user can make communication with the doctor smoothly. As a result, an inspection room can be decided efficiently.

In the inspection room decision support system, the inspection room decision support system may further include a second call control device which is provided for making a call to any one of first call control devices placed in at least part of the inspection rooms. The control unit makes the display device display an operation menu for issuing an instruction to call one of the inspection rooms where the first call control devices are placed, in association with the information about the inspection room. The second call control device communicates with a corresponding one of the first call control devices placed in the inspection room and performs control to enable a call to the first call control device when the instruction to call the inspection room is issued by the operation menu.

With this configuration, when, for example, a user wants to contact a doctor regarding contents of an inspection, the user can call the doctor after the user confirms whether the doctor can talk now or not or which inspection room the doctor is in, based on images. Thus, the user can communicate with the doctor smoothly. As a result, an inspection room can be decided efficiently.

In the inspection room decision support system, the inspection decision support system may further include: an preparation completion information acquiring unit that acquires preparation completion information indicating inspection preparations are completed in the inspection room; a inspection start information acquiring unit that acquires inspection start information indicating an inspection starts in the inspection room; a determination unit that determines a number of persons contained in the data of the captured image on the basis of the data of the captured image captured by the image capturing device of the inspection room; an alert information displaying control unit that makes the display device display alert information indicating an patient is waiting in the inspection room, when a period of the number of persons contained in the data of the captured image being less than two exceeds a threshold in a period between the acquiring of the preparation completion information and the acquiring of the inspection start information.

With this configuration, it is possible to relieve the mental pain of the patient by confirming the patient is waiting a long time in the inspection room after the completion of the preparations for the inspection.

In the disclosed inspection room decision support system, the inspection room decision support system may further include: an preparation completion information acquiring unit that acquires preparation completion information indicating inspection preparations is completed in the inspection room; a inspection start information acquiring unit that acquires inspection start information indicating an inspection starts in the inspection room; an alert information displaying control unit that makes the display device display alert information indicating an patient is waiting in the inspection room, when a period between the acquiring of the preparation completion information and the acquiring of the inspection start information exceeds a threshold.

With this configuration, it is possible to relieve the mental pain of the patient by confirming the patient is waiting a long time in the inspection room after the completion of the preparations for the inspection.

In the inspection room decision support system, the inspection start information may be data of a captured still image firstly captured in the endoscope.

With this configuration, it is possible to automatically detect the start timing of the inspection with simple configuration.

In the inspection room decision support system, the threshold may vary in accordance with at least one of each of regions to be inspected in the inspection room and each of attending doctors in the inspection room.

With this configuration, it is possible to transmit an alert independently of the regions to be inspected and the attending doctors.

In the disclosed inspection room decision support system, the preparation completion information may be data of video transmitted from the endoscope.

With this configuration, it is possible to automatically detect the timing of the completion of the preparations for the inspection with simple configuration.

In the disclosed inspection room decision support system, the information about the endoscope may include information about regions which can be inspected by the endoscope. The inspection room decision support system may further include: a specification unit which specifies inspection rooms in each of which the requested inspection can be conducted, based on contents of the requested inspection and the information about the endoscope; and a notification unit which makes the display device display information so as to notify the outside of the inspection rooms specified by the specification unit.

With this configuration, a user can view the display device to instantly know inspection rooms in each of which a requested inspection can be conducted. Accordingly, the user can select an optimal one from the inspection rooms in each of which the inspection can be conducted, in consideration of congestion states, doctor skills, etc. so that the user can decide an inspection room more promptly.

In the disclosed inspection room decision support system, the registration unit may also register information about medicines which are prepared in each of the inspection rooms in the database. The control unit may read the information about medicines for each of the inspection rooms from the database, and makes the display device display the information about medicines in association with the information about each of the inspection rooms. With this configuration, information about medicines which are prepared in each inspection room together with information about the number of persons waiting for inspection in the inspection room is also displayed on the display device. Accordingly, an optimal inspection room for a requested inspection can be decided based on comprehensive judgment of these pieces of information.

In the inspection room decision support system, the registration unit may also register information about job progress status in each of the inspection rooms into the database. The control unit may read the information about job progress status in each of the inspection rooms from the database, and makes the display device display the information about job progress status in association with the information about each of the inspection rooms.

With this configuration, information about job progress status in each inspection room together with information about the number of persons waiting for inspection in the inspection room is also displayed on the display device. Accordingly, an optimal inspection room for a requested inspection can be decided based on comprehensive judgment of these pieces of information.

In the inspection room decision support method to be performed by a computer for providing support in deciding one inspection room in which a requested endoscopic inspection will be conducted, from a plurality of inspection rooms, the method includes: registering at least information about each of the inspection rooms, information about a number of persons waiting for inspection in each of the inspection rooms and information about an endoscope used in each of the inspection rooms into a database in accordance with the information inputted by an input unit; and controlling by reading at least the information about each of the inspection rooms, the information about the number of persons waiting for inspection in each of the inspection rooms and the information about the endoscope in each of the inspection rooms from the database, and making a display device display these pieces of information associated with each other.

In the inspection room decision support method, the registering step may include registering information about an attending doctor conducting inspection in each of the inspection rooms into the database; and the controlling step may include reading the information about the doctor for each of the inspection rooms from the database, and making the display device display the information about the doctor in association with each of the inspection rooms.

In the inspection room decision support method, the control step may include reading a list of inspection request information about each of the requested inspections from the database, and making the display device display the list of the inspection request information together with the information about each of the inspection rooms. The inspection room decision support method may further include: when (i) one piece of the inspection request information is selected through the input unit from the list of the inspection request information displayed on the display device, and (ii) one piece of the information about each of the inspection rooms is selected through the input unit from the information about each of the inspection rooms displayed on the display device, adding one to the number of persons waiting for inspection in the selected inspection room and registering the added number of persons into the database for updating.

In the inspection room decision support method, the control step may include making the display device display inspection request information excepting inspection request information about a completed inspection from the list of the inspection request information about each of the requested inspection.

In the inspection room decision support method, from the display inspection request information about each of the requested inspection, the control step may include making the display device only display the one piece of the inspection request information selected through the input unit.

In the inspection room decision support method, when (i) one piece of the inspection request information is selected through the input unit from the list of the inspection request information displayed on the display device, and (ii) one piece of the information about each of the inspection rooms is selected through the input unit from the information about each of the inspection rooms displayed on the display device, the control step may include deleting the selected one piece of the inspection request information from a screen of the display device.

In the inspection room decision support method, the inspection room decision support method may further include: acquiring data of captured images from image capturing devices placed in at least part of the inspection rooms respectively, the captured images being obtained by the image capturing devices which capture images of insides of the at least part of the inspection rooms where the image capturing devices are placed. The control step includes making the display device display the data of each captured image captured by a corresponding one of the image capturing devices in each or a selected one of the at least part of the inspection rooms, in association with the information about the inspection room.

In the inspection room decision support method, the control step may include making the display device display an operation menu for issuing an instruction to call one of the inspection rooms where call control devices are placed, in association with the information about the inspection room. The inspection room decision support method may further includes: communicating with a corresponding one of the call control devices placed in the inspection room and performing control to enable a call to the call control device when the instruction to call the inspection room is issued by the operation menu.

In the inspection room decision support method, the inspection room decision support method may further include: acquiring preparation completion information indicating inspection preparations are completed in the inspection room; acquiring inspection start information indicating an inspection starts in the inspection room; determining a number of persons contained in the data of the captured image on the basis of the data of the captured image captured by the image capturing device of the inspection room; and making the display device display alert information indicating an patient is waiting in the inspection room, when a period of the number of persons contained in the data of the captured image being less than two exceeds a threshold in a period between the acquiring of the preparation completion information and the acquiring of the inspection start information.

In the inspection room decision support method, the inspection room decision support method may further include: acquiring preparation completion information indicating inspection preparations is completed in the inspection room; acquiring inspection start information indicating an inspection starts in the inspection room; and making the display device display alert information indicating an patient is waiting in the inspection room, when a period between the acquiring of the preparation completion information and the acquiring of the inspection start information exceeds a threshold.

In the inspection room decision support method, the inspection start information may be data of a captured still image firstly captured in the endoscope.

In the inspection room decision support method, the threshold may vary in accordance with at least one of each of regions to be inspected in the inspection room and each of attending doctors in the inspection room.

In the inspection room decision support method, the preparation completion information may be data of video transmitted from the endoscope.

In the inspection room decision support method, the information about the endoscope may include information about regions which can be inspected by the endoscope. The inspection room decision support method may further include: specifying inspection rooms in each of which the requested inspection can be conducted, based on contents of the requested inspection and the information about the endoscope; and making the display device display information so as to notify the outside of the inspection rooms specified by the specification unit.

In the inspection room decision support method, the inspection room decision support method may further include: registering information about medicines which are prepared in each of the inspection rooms in the database. The control step includes reading the information about medicines for each of the inspection rooms from the database, and making the display device display the information about medicines in association with the information about each of the inspection rooms.

In the inspection room decision support method, the inspection room decision support method may further include: registering information about job progress status in each of the inspection rooms into the database. The control step includes reading the information about job progress status in each of the inspection rooms from the database, and making the display device display the information about job progress status in association with the information about each of the inspection rooms.

A computer readable medium storing a program causes a computer to execute a process for the disclosed inspection room decision support method.

What is claimed is:

1. An inspection room decision support system for providing support in deciding one inspection room in which a requested endoscopic inspection will be conducted, from a plurality of inspection rooms, the system comprising:
   an input unit that inputs information;
   a registration unit that registers at least information about each of the inspection rooms, information about a number of persons waiting for inspection in each of the inspection rooms, information about the number of inspected persons in each of the inspection rooms and information about an endoscope used in each of the inspection rooms into a database in accordance with the information inputted by the input unit; and
   a control unit as a processor, which reads at least the information about each of the inspection rooms, the information about the number of persons waiting for inspection in each of the inspection rooms, the information about the number of inspected persons in each of the inspection rooms and the information about the endoscope in each of the inspection rooms from the database, and makes a display device display these pieces of information associated with each other by using icons for the inspection rooms,
   wherein one of the icons for one of the inspection rooms provides;
   the information about the number of persons waiting for inspection in the one of the inspection rooms on one of right and left sides inside the one of the icons, and
   the information about the number of inspection persons on the one of the inspection rooms on the other of right and left sides inside the one of the icons, and
   the information about the endoscope in each of the inspection rooms on a lower side of the information about the number of persons waiting for inspection and the information about the number of inspected persons inside the one of the icons.

2. The inspection room decision support system according to claim 1, wherein:
   the registration unit further registers information about an attending doctor conducting inspection in each of the inspection rooms into the database; and
   the control unit reads the information about the doctor for each of the inspection rooms from the database, and makes the display device display the information about the doctor in association with each of the inspection rooms.

3. The inspection room decision support system according to claim 1, wherein:
   the control unit reads a list of inspection request information about each of the requested inspections from the database, and makes the display device display the list of the inspection request information together with the information about each of the inspection rooms;
   when (i) one piece of the inspection request information is selected through the input unit from the list of the inspection request information displayed on the display device, and (ii) one piece of the information about each of the inspection rooms is selected through the input unit from the information about each of the inspection rooms displayed on the display device, the registration unit adds one to the number of persons waiting for inspection in the selected inspection room and registers the added number of persons into the database for updating.

4. The inspection room decision support system according to claim 3, wherein:
   the control unit makes the display device display inspection request information excepting inspection request information about a completed inspection from the list of the inspection request information about each of the requested inspection.

5. The inspection room decision support system according to claim 3, wherein:
   from the display inspection request information about each of the requested inspection, the control unit makes the display device only display the one piece of the inspection request information selected through the input unit.

6. The inspection room decision support system according to claim 3, wherein:
   when (i) one piece of the inspection request information is selected through the input unit from the list of the inspection request information displayed on the display device, and (ii) one piece of the information about each of the inspection rooms is selected through the input unit from the information about each of the inspection rooms displayed on the display device, the control unit deletes the selected one piece of the inspection request information from a screen of the display device.

7. The inspection room decision support system according to claim 1, further comprising:
a captured image data acquisition unit that acquires data of captured images from image capturing devices placed in at least part of the inspection rooms respectively, the captured images being obtained by the image capturing devices which capture images of insides of the at least part of the inspection rooms where the image capturing devices are placed; wherein:
the control unit makes the display device display the data of each captured image captured by a corresponding one of the image capturing devices in each or a selected one of the at least part of the inspection rooms, in association with the information about the inspection room.

8. The inspection room decision support system according to claim 7, further comprising:
a second call control device which is provided for making a call to any one of first call control devices placed in at least part of the inspection rooms; wherein:
the control unit makes the display device display an operation menu for issuing an instruction to call one of the inspection rooms where the first call control devices are placed, in association with the information about the inspection room; and
the second call control device communicates with a corresponding one of the first call control devices placed in the inspection room and performs control to enable a call to the first call control device when the instruction to call the inspection room is issued by the operation menu.

9. The inspection room decision support system according to claim 7, further comprising:
a preparation completion information acquiring unit that acquires preparation completion information indicating inspection preparations are completed in the inspection room;
an inspection start information acquiring unit that acquires inspection start information indicating an inspection starts in the inspection room;
a determination unit that determines a number of persons contained in the data of the captured image on the basis of the data of the captured image captured by the image capturing device of the inspection room;
an alert information displaying control unit that makes the display device display alert information indicating a patient is waiting in the inspection room, when a period of the number of persons contained in the data of the captured image being less than two exceeds a threshold in a period between the acquiring of the preparation completion information and the acquiring of the inspection start information.

10. The inspection room decision support system according to claim 9, the preparation completion information is data of video transmitted from the endoscope.

11. The inspection room decision support system according to claim 1, further comprising:
a preparation completion information acquiring unit that acquires preparation completion information indicating inspection preparations is completed in the inspection room;
an inspection start information acquiring unit that acquires inspection start information indicating an inspection starts in the inspection room;
an alert information displaying control unit that makes the display device display alert information indicating a patient is waiting in the inspection room, when a period between the acquiring of the preparation completion information and the acquiring of the inspection start information exceeds a threshold.

12. The inspection room decision support system according to claim 11, wherein:
the inspection start information is data of a captured still image firstly captured in the endoscope.

13. The inspection room decision support system according to claim 11, wherein:
the threshold varies in accordance with at least one of each of regions to be inspected in the inspection room and each of attending doctors in the inspection room.

14. The inspection room decision support system according to claim 1, wherein:
the information about the endoscope includes information about regions which can be inspected by the endoscope; and
the system further comprises:
a specification unit which specifies inspection rooms in each of which the requested inspection can be conducted, based on contents of the requested inspection and the information about the endoscope; and
a notification unit which makes the display device display information so as to notify the outside of the inspection rooms specified by the specification unit.

15. The inspection room decision support system according to claim 1, wherein:
the registration unit also registers information about medicines which are prepared in each of the inspection rooms in the database; and
the control unit reads the information about medicines for each of the inspection rooms from the database, and makes the display device display the information about medicines in association with the information about each of the inspection rooms.

16. The inspection room decision support system according to claim 1, wherein:
the registration unit also registers information about job progress status in each of the inspection rooms into the database; and
the control unit reads the information about job progress status in each of the inspection rooms from the database, and makes the display device display the information about job progress status in association with the information about each of the inspection rooms.

17. An inspection room decision support method to be performed by a computer for providing support in deciding one inspection room in which a requested endoscopic inspection will be conducted, from a plurality of inspection rooms, the method comprising:
registering at least information about each of the inspection rooms, information about a number of persons waiting for inspection in each of the inspection rooms, information about the number of inspected persons in each of the inspection rooms and information about an endoscope used in each of the inspection rooms into a database in accordance with the information inputted by an input unit; and
controlling by reading at least the information about each of the inspection rooms, the information about the number of persons waiting for inspection in each of the inspection rooms, the information about the number of inspected persons in each of the inspection rooms and the information about the endoscope in each of the inspection rooms from the database, and making a display device display these pieces of information associated with each other by using icons for the inspection rooms, wherein one the icons for one of the inspection rooms provides;

the information about the number of persons waiting for inspection in the one of the inspection rooms on one of right and left sides inside the one of the icons, and the information about the number of inspected persons on the one of the inspection rooms on the other of right and left sides inside the one of the icons, and the information about the endoscope in each of the inspection rooms on a lower side of the formation about the number of persons waiting for inspection and the information about the number of inspected persons inside the one of the icons.

18. The inspection room decision support method according to claim 17, wherein:

the registering step includes registering information about an attending doctor conducting inspection in each of the inspection rooms into the database; and the controlling step includes reading the information about the doctor for each of the inspection rooms from the database, and making the display device display the information about the doctor in association with each of the inspection rooms.

19. The inspection room decision support method according to claim 17, wherein:

the control step includes reading a list of inspection request information about each of the requested inspections from the database, and making the display device display the list of the inspection request information together with the information about each of the inspection rooms; and the inspection room decision support method further comprises: when (i) one piece of the inspection request information is selected through the input unit from the list of the inspection request information displayed on the display device, and (ii) one piece of the information about each of the inspection rooms is selected through the input unit from the information about each of the inspection rooms displayed on the display device, adding one to the number of persons waiting for inspection in the selected inspection room and registering the added number of persons into the database for updating.

20. The inspection room decision support method according to claim 19, wherein:

the control step includes making the display device display inspection request information excepting inspection request information about a completed inspection from the list of the inspection request information about each of the requested inspection.

21. The inspection room decision support method according to claim 19, wherein:

from the display inspection request information about each of the requested inspection, the control step includes making the display device only display the one piece of the inspection request information selected through the input unit.

22. The inspection room decision support method according to claim 19, wherein:

when (i) one piece of the inspection request information is selected through the input unit from the list of the inspection request information displayed on the display device, and (ii) one piece of the information about each of the inspection rooms is selected through the input unit from the information about each of the inspection rooms displayed on the display device, the control step includes deleting the selected one piece of the inspection request information from a screen of the display device.

23. The inspection room decision support method according to claim 17, further comprising:

acquiring data of captured images from image capturing devices placed in at least part of the inspection rooms respectively, the captured images being obtained by the image capturing devices which capture images of insides of the at least part of the inspection rooms where the image capturing devices are placed; wherein:

the control step includes making the display device display the data of each captured image captured by a corresponding one of the image capturing devices in each or a selected one of the at least part of the inspection rooms, in association with the information about the inspection room.

24. The inspection room decision support method according to claim 23, wherein:

the control step includes making the display device display an operation menu for issuing an instruction to call one of the inspection rooms where call control devices are placed, in association with the information about the inspection room; and the inspection room decision support method further includes:

communicating with a corresponding one of the call control devices placed in the inspection room and performing control to enable a call to the call control device when the instruction to call the inspection room is issued by the operation menu.

25. The inspection room decision support method according to claim 23, further comprising:

acquiring preparation completion information indicating inspection preparations are completed in the inspection room;

acquiring inspection start information indicating an inspection starts in the inspection room;

determining a number of persons contained in the data of the captured image on the basis of the data of the captured image captured by the image capturing device of the inspection room; and making the display device display alert information indicating a patient is waiting in the inspection room, when a period of the number of persons contained in the data of the captured image being less than two exceeds a threshold in a period between the acquiring of the preparation completion information and the acquiring of the inspection start information.

26. The inspection room decision support method according to claim 25, the preparation completion information is data of video transmitted from the endoscope.

27. The inspection room decision support method according to claim 17, further comprising:

acquiring preparation completion information indicating inspection preparations is completed in the inspection room;

acquiring inspection start information indicating an inspection starts in the inspection room; and making the display device display alert information indicating a patient is waiting in the inspection room, when a period between the acquiring of the preparation completion information and the acquiring of the inspection start information exceeds a threshold.

28. The inspection room decision support method according to claim 27, wherein:

the inspection start information is data of a captured still image firstly captured in the endoscope.

29. The inspection room decision support method according to claim 27, wherein:

the threshold varies in accordance with at least one of each of regions to be inspected in the inspection room and each of attending doctors in the inspection room.

30. The inspection room decision support method according to claim 17, wherein:
the information about the endoscope includes information about regions which can be inspected by the endoscope; and the inspection room decision support method further comprises:

specifying inspection rooms in each of which the requested inspection can be conducted, based on contents of the requested inspection and the information about the endoscope; and making the display device display information so as to notify the outside of the inspection rooms specified by the specification unit.

31. The inspection room decision support method according to claim 17, further comprising:
registering information about medicines which are prepared in each of the inspection rooms in the database, wherein:
the control step includes reading the information about medicines for each of the inspection rooms from the database, and making the display device display the information about medicines in association with the information about each of the inspection rooms.

32. The inspection room decision support method according to claim 17, further comprising:
registering information about job progress status in each of the inspection rooms into the database, wherein:
the control step includes reading the information about job progress status in each of the inspection rooms from the database, and making the display device display the information about job progress status in association with the information about each of the inspection rooms.

33. A non-transitory computer readable medium storing a program causing a computer to execute a process for providing support in deciding one inspection room in which a requested endoscopic inspection will be conducted, from a plurality of inspection rooms, the process comprising:
registering at least information about each of the inspection rooms, information about a number of persons waiting for inspection in each of the inspection rooms, information about the number of inspected persons in each of the inspection rooms and information about an endoscope used in each of the inspection rooms into a database in accordance with the information inputted by an input unit; and controlling by reading at least the information about each of the inspection rooms, the information about the number of persons waiting for inspection in each of the inspection rooms, the information about the number of inspected persons in each of the inspection rooms and the information about the endoscope in each of the inspection rooms from the database, and making a display device display these pieces of information associated with each other by using icons for the inspection rooms, wherein one of the icons for one of the inspection rooms provides:

the information about the number of persons waiting for inspection in the one of the inspection rooms on one of right and left sides inside the one of the icons, and the information about the number of inspected persons on the one of the inspection rooms on the other of right and left sides inside the one of the icons, and the information about the endoscope in each of the inspection rooms on a lower side of the information about the number of persons waiting for inspection and the information about the number of inspected persons inside the one of the icons.

* * * * *